(12) United States Patent
Kreader

(10) Patent No.: US 10,711,266 B2
(45) Date of Patent: *Jul. 14, 2020

(54) MICRO RNA ISOLATION FROM A BIOLOGICAL SAMPLE

(71) Applicant: SIGMA-ALDRICH CO. LLC, St. Louis, MO (US)

(72) Inventor: Carol A. Kreader, St. Louis, MO (US)

(73) Assignee: Sigma-Aldrich Co. LLC, St. Louis, MO (US)

(*) Notice: Subject to any disclaimer, the term of this patent is extended or adjusted under 35 U.S.C. 154(b) by 69 days.

This patent is subject to a terminal disclaimer.

(21) Appl. No.: 16/160,363

(22) Filed: Oct. 15, 2018

(65) Prior Publication Data

US 2019/0144850 A1 May 16, 2019

Related U.S. Application Data

(63) Continuation of application No. 15/038,967, filed as application No. PCT/US2014/067321 on Nov. 25, 2014, now Pat. No. 10,131,902.

(60) Provisional application No. 61/909,834, filed on Nov. 27, 2013.

(51) Int. Cl.
| | |
|---|---|
| C12N 15/00 | (2006.01) |
| C12N 15/10 | (2006.01) |
| C12Q 1/68 | (2018.01) |
| G01N 33/53 | (2006.01) |
| G01N 33/566 | (2006.01) |
| C07H 1/08 | (2006.01) |
| C12Q 1/6804 | (2018.01) |

(52) U.S. Cl.
CPC ........... *C12N 15/1013* (2013.01); *C07H 1/08* (2013.01); *C12Q 1/68* (2013.01); *C12Q 1/6804* (2013.01); *G01N 33/53* (2013.01); *G01N 33/566* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 9,753,007 B1* | 9/2017 | Chambers | B01D 57/02 |
| 2011/0287412 A1* | 11/2011 | Landthaler | C12N 15/1058 435/6.1 |
| 2013/0197206 A1* | 8/2013 | Nishibu | C12Q 1/6804 536/23.1 |
| 2014/0163089 A1 | 6/2014 | Chen et al. | |
| 2015/0301058 A1* | 10/2015 | Schettini | A61K 39/0011 424/193.1 |

(Continued)

FOREIGN PATENT DOCUMENTS

| | | |
|---|---|---|
| WO | 2012/115885 A1 | 8/2012 |
| WO | 2015/094609 A1 | 6/2015 |

OTHER PUBLICATIONS

Jaskiewicz et al. (Argonaute CLIP—a method to identify in vivo targets of miRNAs, Methods. Oct. 2012;58(2): Epub Sep. 27, 2012).*

(Continued)

*Primary Examiner* — Aaron A Priest
(74) *Attorney, Agent, or Firm* — Benjamin J. Sodey; Sigma-Aldrich Co. LLC

(57) ABSTRACT

The present disclosure provides methods and kits for isolating miRNAs from biological fluids.

11 Claims, 15 Drawing Sheets

(56) References Cited

U.S. PATENT DOCUMENTS

2016/0159846 A1 6/2016 Prakash et al.
2016/0289734 A1 10/2016 Zamore et al.

OTHER PUBLICATIONS

Jensen, et al., "CLIP: Crosslinking and ImmunoPrecipitation of In Vivo RNA Targets of RNA-Binding Proteins", Methods in Molecular Biology, vol. 488, 2008, pp. 85-98.

Jaskiewicz et al., "Argonaute CLIP—a method to identify in vivo targets of miRNAs, Methods", Oct. 2012;58(2): Epub Sep. 27, 2012, 7 pages.

Arroyo et al., "Argonaute2 complexes carry a population of circulating microRNAs independent of vesicles in human plasma," PNAS, 2011, vol. 108, No. 12, pp. 5003-5008.

Fichtlscherer et al., "Circulating MicroRNAs in Patients With Coronary Artery Disease," Circulation Research, 2010, 15 pages.

Gallo et al., "The Majority of MicroRNAs Detectable in Serum and Saliva Is Concentrated in Exosomes," PLoS ONE, 2012, e30679, vol. 7, No. 3, pp. 1-5.

International Search Report and Written Opinion received for PCT Application No. PCT/US2014/67321, dated Apr. 7, 2015, 12 pages.

Kim et al., "Plasma Components Affect Accuracy of Circulating Cancer-Related MicroRNA Quantitation," The Journal of Molecular Diagnostics, 2012, vol. 14, No. 1, pp. 71-80.

Kreader, "Ago RIP to Isolate microRNA and their Targets Using Imprint RNA Immunoprecipitation Kit," Sigma-Aldrich, "Enabling Science to Improve the Quality of Life," 2013, 3 pages.

MBL_RIP, RIP-Assay Kit for miRNA, MBL, 2012 (online). Retrieved on Jan. 1, 2015, 2 pages.

Turchinovich et al., "Characterization of extracellular circulating microRNA," Nucleic Acids Research, 2011, vol. 39, No. 16, pp. 7223-7233.

International Preliminary Report on Patentability received for PCT Application No. PCT/US2014/67321, dated Jun. 9, 2016, 7 pages.

\* cited by examiner

MICRO RNA ISOLATION FROM A BIOLOGICAL SAMPLE

CROSS-REFERENCE TO RELATED APPLICATIONS

This application is a continuation of Application Ser. No. 15/038,967 filed May 24, 2016, which is a U.S. National Stage Application of PCT International Application No. PCT/US2014/067321, filed Nov. 25, 2014, which claims priority to U.S. Provisional Pat. App. Ser. No. 61/985,000, filed Apr. 28, 2014, and U.S. Provisional Pat. App. Ser. No. 61/909,834, filed Nov. 27, 2013, the disclosure of each of which is hereby incorporated by reference in its entirety.

FIELD OF THE INVENTION

The present disclosure relates to means for isolating microRNAs from biological fluids.

BACKGROUND

MicroRNAs (miRNAs) are small, noncoding RNAs that influence gene regulatory networks by post-transcriptional regulation of specific messenger RNA (mRNA) targets via specific base-pairing interactions. miRNAs have been shown to be present in human biofluids in a cell-free form. These cell-free miRNAs may be non-vesicular, bound and protected by proteins in miRNA-protein complexes, enclosed in membrane-bound vesicles such as exosomes or microvesicles, or both. Given the important functional role of miRNA in disease, this set of nucleic acid molecules contains candidates for diagnosing and prognosing disease, and monitoring response to therapies in a wide variety of patients and in subjects prior to manifesting disease in a readily available biological sample, such as blood serum and plasma, urine, or saliva. Current methods of isolating miRNAs are directed to relatively abundant miRNAs in cells and tissues, use spin columns which are not readily automated or scaled up, are complicated and involve toxic compounds, or may specifically isolate either vesicular or non-vesicular miRNAs. Furthermore, miRNAs of diagnostic or prognostic interest are often present at low abundance in biofluids, making their detection using current isolation methods challenging. Therefore, there is a need for a simple, efficient, automatable, and scalable method for isolating all or a majority of miRNAs in biofluids.

SUMMARY OF THE INVENTION

One aspect of the present disclosure provides a method for isolating microRNA (miRNA) from a biological fluid. The method comprises contacting the biological fluid with a surface active agent and an anti-miRNA-binding protein reagent, wherein the surface active agent dissociates biological fluid components and the anti-miRNA-binding protein reagent interacts with a miRNA-binding protein associated with miRNA to form immunoprecipitated miRNA complexes. The method further comprises releasing miRNA from the immunoprecipitated miRNA complexes.

Another aspect of the disclosure encompasses a kit for isolating microRNA from a biological fluid. The kit comprises a surface active agent, an anti-miRNA-binding protein reagent, and a miRNA releasing reagent.

Other aspects and iterations of the disclosure are described in more detail below.

DETAILED DESCRIPTION OF THE INVENTION

Figure 1:
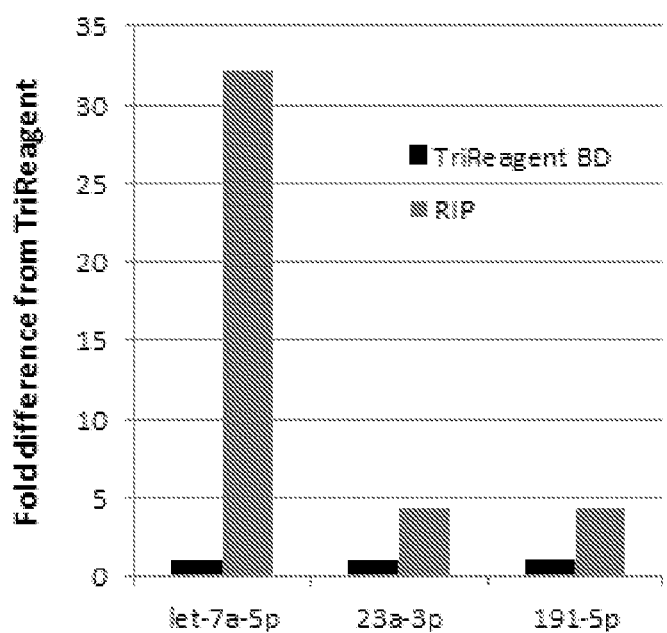
FIG. 1 presents two plots comparing miRNA isolation from 0.2 ml plasma using Tri Reagent® BD or RNA immunoprecipitation (RIP). The amounts of isolated miRNA by RIP are presented as the fold difference from miRNA isolated using Tri Reagent® BD. (A) depicts the levels of let-7a-5p, 23a-3p, and 191-5p miRNAs, and (B) shows the levels of 142-3p and 451a miRNAs.
Figure 1:
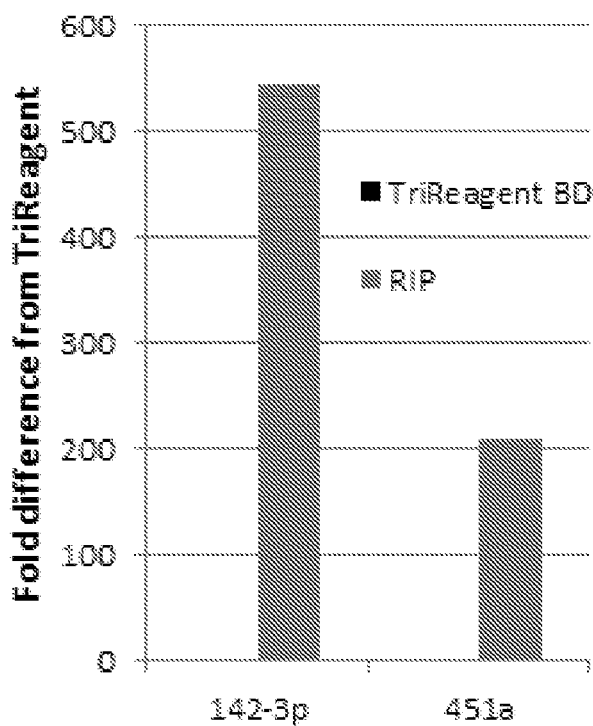

An efficient and rapid method for isolating circulating miRNAs has been discovered. As illustrated in the examples, a method of the disclosure can simultaneously isolate both vesicle-associated and non-vesicle associated circulating miRNAs. Advantageously, the methods and kits of the present disclosure allow for the rapid and specific isolation of pure preparations of miRNAs with no contamination by other types of RNA. Additionally, the methods and kits disclosed herein allow for isolation of miRNAs in high yield from dilute extracellular fluids. Moreover, methods of the present invention are scalable, allowing miRNA isolation from increasing volumes of extracellular biological fluids.

Levels of miRNAs are correlated with disease, including cancer, cardiovascular disease, and in numerous other diseases and developmental processes, including schizophrenia, Alzheimer's disease, immune cell development and modulation of both adaptive and innate immunity, stem cell maintenance and pluripotency, nervous system development, endocrine disease, including diabetes, development of the pancreas, Fragile X Syndrome, cutaneous wound healing, cell cycle progression, transplanted tissue rejection, hypoxia, skeletal muscle differentiation. Additionally, miRNAs also are expressed by viruses, and target genes of those miRNA have been identified. As such, methods and kits of the present disclosure can be used to prepare miRNA for assays to diagnose diseases or disease states using a readily available biological sample, such as blood, serum, or plasma.

I. Method

The present disclosure encompasses a method for isolating microRNA (miRNA) from a biological fluid. The method comprises contacting the biological fluid with a surface active agent and an anti-miRNA-binding protein reagent. The surface active agent dissociates biological fluid components and the anti-miRNA-binding protein reagent interacts with miRNA-binding protein(s) associated with miRNA to form immunoprecipitated miRNA complexes. The method further comprises releasing miRNA from the immunoprecipitated miRNA complexes.

The method disclosed herein specifically isolates miRNAs. As detailed in Example 12 below, other types of small RNAs (such as small nuclear RNAs or small nucleolar RNAs) are not isolated by the disclosed method, and larger RNA molecules (such as messenger RNAs or ribosomal RNAs) are not isolated by the disclosed method.

(a) Biological Fluid

A method of the present disclosure comprises isolation of extracellular circulating miRNA in a biological fluid sample obtained from a subject. The term "subject," as used herein, refers to a human or an animal. The subject can be an embryo, a juvenile, or an adult. The subject can be male or female. Suitable animals include vertebrates such as mammals, birds, reptiles, amphibians, and fish. Examples of suitable mammals include, without limit, rodents, companion animals, livestock, and primates. Non-limiting examples of rodents include mice, rats, hamsters, gerbils, and guinea pigs. Suitable companion animals include, but are not limited to, cats, dogs, rabbits, hedgehogs, and ferrets. Non-limiting examples of livestock include horses, goats, sheep, swine, cattle, llamas, and alpacas. Suitable primates include, but are not limited to, capuchin monkeys, chimpanzees, lemurs, macaques, marmosets, tamarins, spider monkeys, squirrel monkeys, and vervet monkeys. Non-limiting examples of birds include chickens, turkeys, ducks, and geese. An exemplary subject is a human.

The term "biological fluid" can refer to all biological fluids and excretions isolated from any given subject. Non-limiting examples of a biological fluid can include blood and fractions thereof, blood serum, blood plasma, urine, excreta, semen, seminal fluid, seminal plasma, prostatic fluid, pre-ejaculatory fluid (Cowper's fluid), pleural effusion, tears, saliva, sputum, sweat, biopsy, ascites, cerebrospinal fluid, amniotic fluid, lymph, marrow, cervical secretions, vaginal secretions, endometrial secretions, gastrointestinal secretions, bronchial secretions, breast secretions, ovarian cyst secretions, tissue fluid, tumor aspirant, and tissue fluid samples. In some embodiments, a biological fluid is blood serum. In other embodiments, a biological fluid is blood plasma.

Methods of obtaining a blood plasma or serum sample from a subject are well known in the art. For instance, venipuncture, with or without a catheter, may be used to collect a blood sample for preparing serum. Methods of preparing plasma and serum from a blood sample are known in the art. In general, a blood sample is large enough to supply sufficient amounts of plasma or serum to be processed as described further below. A plasma or serum sample may be processed immediately after collecting the sample. Alternatively, a plasma or serum sample may be frozen for later processing.

A biological fluid sample can be obtained from a subject by freshly collecting a sample. Alternatively, a biological fluid sample can be obtained from a previously collected and stored sample. For instance, when a biological fluid is blood plasma or serum, a sample can be obtained from a collection of stored and preserved blood samples. In some embodiments, a sample is obtained by freshly collecting a sample. In other embodiments, a sample is obtained from a previously collected and stored sample.

In some embodiments, a biological fluid sample is undiluted. In other embodiments, a biological fluid sample is diluted before isolation of miRNA. The degree of dilution may depend on a number of factors including but not limited to the miRNA, the type of biological fluid in the sample, the subject, the disease condition of the subject, the type of assay used to measure the miRNA, and the reagents utilized in the assay used to measure the miRNA. In one embodiment, a biological fluid sample is diluted by adding a volume of diluent ranging from about ½ of the original sample volume to about 50,000 times the original sample volume. The diluent may be any fluid that does not interfere with miRNA isolation or other methods used in subsequent processing steps. Non-limiting examples of suitable diluents include deionized water, distilled water, saline solution, Ringer's solution, phosphate buffered saline solution, TRIS-buffered saline solution, standard saline citrate, and HEPES-buffered saline.

(b) Surface Active Agent

A biological fluid is contacted with a surface active agent (alternatively referred to as a "surfactant" or "detergent"). As used herein, the term "surface active agent" can be used to describe any agent capable of dissociating biological fluid components that can comprise a circulating miRNA. Non-limiting examples of biological fluid components that can comprise a circulating miRNA include extracellular vesicles such as lipoproteins, exosomes, microvesicles, ectosomes, apoptotic bodies, and other extracellular vesicles.

As will be appreciated by a skilled artisan, any surface active agent capable of dissociating biological fluid components can be used in methods of the disclosure, provided that the surface active agent does not interfere with formation of an immunoprecipitated miRNA complex of the disclosure. For instance, a surface active agent can be an anionic surface active agent, a cationic surface active agent, a zwitterionic surface active agent, a non-ionic surface active agent, or combinations thereof. The identity of the surface active agent of the invention can and will vary, depending upon the identity of the biological fluid components in a biological fluid that may comprise a circulating miRNA, the anti-miRNA-binding protein reagent, and the isolated miRNA.

In some embodiments, a surface active agent is an anionic surface active agent. Suitable anionic surface active agents include, but are not limited to, amine dodecylbenzene sulfonate; ammonium capryleth sulfate; ammonium cumenesulfonate; ammonium dihydroxy stearate; ammonium dodecylbenzene sulfonate; ammonium laureth sulfate; ammonium laureth-12 sulfate; ammonium laureth-30 sulfate; ammonium lauryl sarcosinate; ammonium lauryl sulfate; ammonium lauryl sulfosuccinate; ammonium lignosulfonate; ammonium myreth sulfate; ammonium naphthalene sulfonate; ammonium nonoxynol-20 sulfate; ammonium nonoxynol-30 sulfate; ammonium nonoxynol-4 sulfate; ammonium nonoxynol-6 sulfate; ammonium nonoxynol-9 sulfate; ammonium oleic sulfate; ammonium perfluorooctanoate; ammonium stearate; ammonium xylenesulfonate; butyl naphthalene sulfonate; butyl phosphate; calcium dodecylbenzene sulfonate; calcium stearoyl lactylate; calcium tetrapropylenebenzene sulfonate; capryleth-9 carboxylic acid; cetyl phosphate; cumene sulfonic acid; DEA-cetyl phosphate; DEA-dodecylbenzene sulfonate; DEA-lauryl sulfate; deceth-4 phosphate; diammonium lauryl sulfosuccinate; diammonium stearyl sulfosuccinamate; diamyl sodium sulfosuccinate; dicyclohexyl sodium sulfosuccinate; dihexyl sodium sulfosuccinate; diisobutyl sodium sulfosuccinate; dilaureth-7 citrate; dimethiconol; dinonoxynol-4 phosphate; dioctyl ammonium sulfosuccinate; dioctyl sodium sulfosuccinate; disodium cetearyl sulfosuccinamate; disodium cocamido MEA-sulfosuccinate; disodium cocamido PEG-3 sulfosuccinate; disodium deceth-6 sulfosuccinate; disodium decyl diphenyl ether disulfonate; disodium dodecyloxy propyl sulfosuccinamate; disodium isodecyl sulfosuccinate; disodium laneth-5 sulfosuccinate; disodium lauramido DEA-sulfosuccinate; disodium lauramido MEA-sulfosuccinate; disodium laureth sulfosuccinate; disodium lauryl sulfosuccinate; disodium myristamido MEA-sulfosuccinate; disodium oleamido MEA-sulfosuccinate; disodium oleamido PEG-2 sulfosuccinate; disodium oleth-3 sulfosuccinate; disodium PEG-4 cocamido MIPA sulfosuccinate; disodium ricinoleamido MEA-sulfosuccinate; disodium stearyl sulfosuccinamate; disodium undecylenamido MEA-sulfosuccinate; ditridecyl sodium sulfosuccinate; dodecenylsuccinic anhydride; dodecyl diphenyl ether disulfonic acid; dodecyl diphenyloxide disulfonic acid; dodecylbenzenesulfonic acid; glyceryl dioleate SE; glyceryl distearate SE; glyceryl ricinoleate SE; glyceryl stearate citrate; glyceryl stearate SE; glycol stearate SE; hexyl phosphate; isopropyl phosphate; isopropylamine dodecylbenzenesulfonate; isosteareth-2 phosphate; isotrideceth-3 phosphate; isotrideceth-6 phosphate; laureth-1 phosphate; laureth-12 carboxylic acid; laureth-3 phosphate; laureth-4 phosphate; laureth-6 phosphate; laureth-7 citrate; laureth-9 phosphate; lauryl phosphate; lithium lauryl sulfate; magnesium laureth sulfate; magnesium PEG-3 cocamide sulfate; MEA-laureth phosphate; MEA-lauryl sulfate; MIPA-laureth sulfate; MIPA-lauryl sulfate; myristoyl sarcosine; naphthalene-formaldehyde sulfonate; nonoxynol-10 phosphate; nonoxynol-12 phosphate; nonoxynol-3 phosphate; nonoxynol-4 phosphate; nonoxynol-4 sulfate; nonoxynol-6 phosphate; nonoxynol-7 phosphate; nonoxynol-8 phosphate; nonoxynol-9 phosphate; nonyl nonoxynol-10 phosphate; nonyl nonoxynol-15 phosphate; nonyl nonoxynol-7 phosphate; oleth-10 carboxylic acid; oleth-10 phosphate; oleth-3 carboxylic acid; oleth-4 phosphate; oleth-5 phosphate;

oleth-6 carboxylic acid; oleth-7 phosphate; PEG-2 dilaurate SE; PEG-2 dioleate SE; PEG-2 distearate SE; PEG-2 laurate SE; PEG-2 oleate SE; PEG-2 stearate SE; PEG-9 stearamide carboxylic acid; potassium cetyl phosphate; potassium deceth-4 phosphate; potassium dodecylbenzene sulfonate; potassium isosteareth-2 phosphate; potassium lauroyl sarcosinate; potassium lauryl sulfate; potassium oleate; potassium oleic sulfate; potassium perfluorooctoate; potassium ricinoleic sulfate; PPG-2 laurate SE; PPG-2 oleate SE; PPG-2 stearate SE; PPG-5-ceteth-10 phosphate; propylene glycol laurate SE; propylene glycol oleate SE; propylene glycol ricinoleate SE; propylene glycol stearate SE; PVM/MA copolymer; sodium 2-ethylhexyl phosphate; sodium 2-ethylhexyl sulfate; sodium a olefin sulfonate; sodium allyloxy hydroxypropyl sulfonate; sodium behenoyl lactylate; sodium butoxyethoxy acetate; sodium butyl naphthalene sulfonate; sodium butyl oleate sulfate; sodium butyl oleate sulfonate; sodium butyl phosphate; sodium caproyl lactylate; sodium caprylyl sulfonate; sodium cetyl sulfate; sodium cholate; sodium cumenesulfonate; sodium deceth sulfate; sodium decyl diphenyl ether sulfonate; sodium decyl sulfate; sodium deoxycholate; sodium dibutyl naphthalene sulfonate; sodium didodecylbenzene sulfonate; sodium diisooctyl sulfosuccinate; sodium diisopropyl naphthalene sulfonate; sodium dilaureth-7 citrate; sodium dinonyl sulfosuccinate; sodium dodecyl diphenyl ether disulfonate; sodium dodecyl diphenyloxide disulfonate; sodium dodecylbenzenesulfonate; sodium glyceryl trioleate sulfate; sodium hexadecyl diphenyl disulfonate; sodium hexadecyl diphenyloxide disulfonate; sodium hexyl diphenyloxide disulfonate; sodium isothionate; sodium isodecyl sulfate; sodium isooctyl sulfate; sodium isostearoyl lactylate; sodium isotrideceth-15 sulfate; sodium lactate; sodium lauramido DEA-sulfosuccinate; sodium laureth phosphate; sodium laureth sulfate; sodium laureth sulfosuccinate; sodium laureth-10 phosphate; sodium laureth-11 carboxylate; sodium laureth-12 sulfate; sodium laureth-13 acetate; sodium laureth-13 carboxylate; sodium laureth-3 carboxylate; sodium laureth-4 carboxylate; sodium laureth-4 phosphate; sodium laureth-6 carboxylate; sodium laureth-7 carboxylate; sodium laureth-7 sulfate; sodium laureth-8 sulfate; sodium lauroyl glutamate; sodium lauroyl lactylate; sodium lauroyl lactylate; sodium lauroyl methylaminopropionate; sodium lauroyl sarcosinate; sodium lauryl phosphate; sodium lauryl sulfate; sodium lauryl sulfoacetate; sodium lignate; sodium lignosulfonate; sodium methallyl sulfonate; sodium methyl lauroyl taurate; sodium methyl myristoyl taurate; sodium methyl oleoyl taurate; sodium methyl palmitoyl taurate; sodium methyl stearoyl taurate; sodium methylnaphthalenesulfonate; sodium m-nitrobenzenesulfonate; sodium myreth sulfate; sodium myristoyl glutamate; sodium myristoyl sarcosinate; sodium myristyl sulfate; sodium nonoxynol sulfate; sodium nonoxynol-10 sulfate; sodium nonoxynol-10 sulfosuccinate; sodium nonoxynol-15 sulfate; sodium nonoxynol-4 sulfate; sodium nonoxynol-5 sulfate; sodium nonoxynol-6 phosphate; sodium nonoxynol-6 sulfate; sodium nonoxynol-8 sulfate; sodium nonoxynol-9 phosphate; sodium nonoxynol-9 sulfate; sodium octoxynol-2 ethane sulfonate; sodium octoxynol-3 sulfate; sodium octyl sulfate; sodium octylphenoxyethoxyethyl sulfonate; sodium oleic sulfate; sodium oleth-7 phosphate; sodium oleyl phosphate; sodium oleyl sulfate; sodium oleyl sulfosuccinamate; sodium palmitoyl sarcosinate; sodium phenyl sulfonate; sodium propyl oleate sulfate; sodium stearoyl lactylate; sodium stearyl sulfosuccinamate; sodium trideceth sulfate; sodium trideceth-3 carboxylate; sodium trideceth-6 carboxylate; sodium trideceth-7 carboxylate; sodium tridecyl sulfate; sodium tridecylbenzene sulfonate; sodium xylenesulfonate; stearoyl sarcosine; TEA-lauroyl glutamate; TEA-lauryl sulfate; tetrasodium dicarboxyethyl stearyl sulfosuccinamate; TIPA-laureth sulfate; triceteareth-4 phosphate; triceteth-5 phosphate; trideceth-2 phosphate; trideceth-3 phosphate; trideceth-5 phosphate; tridecyl phosphate; and trilaureth-4 phosphate; and trioctyl phosphate.

In other embodiments, a surface active agent is a cationic surface active agent. Examples of suitable cationic surface active agents include, but are not limited to, alkyltrimethylammonium bromide; benzalkonium chloride; benzalkonium chloride; benzyldimethylhexadecylammonium chloride; benzyldimethyltetradecylammonium chloride; benzyldodecyldimethylammonium bromide; benzyltrimethylammonium tetrachloroiodate; cetyltrimethylammonium bromide (CTAB); dimethyldioctadecylammonium bromide; dodecylethyldimethylammonium bromide; dodecyltrimethylammonium bromide; dodecyltrimethylammonium bromide; dodecyltrimethylammonium chloride; ethylhexadecyldimethylammonium bromide; Girard's reagent T; hexadecyltrimethylammonium bromide; hexadecyltrimethylammonium bromide; N,N',N'-polyoxyethylene(10)-N-tallow-1,3-diaminopropane; thonzonium bromide; and trimethyl(tetradecyl)ammonium bromide.

In yet other embodiments, a surface active agent is a zwitterionic surface active agent. Suitable zwitterionic surface active agents include, but are not limited to, 3-[(3-cholamidopropyl)dimethylammonio]-2-hydroxy-1-propanesulfonate (CHAPSO); 3-[(3-cholamidopropyl) dimethylammonio]-1-propanesulfonate (CHAPS); 3-(4-Heptyl)phenyl-3-hydroxypropyl) dimethylammoniopropanesulfonate (C7BzO); 3-(N,N-dimethyloctylammonio) propanesulfonate inner salt (SB3-8); 3-(decyldimethylammonio) propanesulfonate inner salt (SB3-10; caprylyl sulfobetaine); 3-(dodecyldimethylammonio) propanesulfonate inner salt (SB3-12); 3-(N,N-dimethyltetradecylammonio)propanesulfonate (SB3-14); 3-(N,N-dimethylpalmitylammonio) propanesulfonate (SB3-16); 3-(N,N-dimethyloctadecylammonio) propanesulfonate (SB3-18); 3-[N,N-dimethyl(3-myristoylaminopropyl)ammonio]propanesulfonate (ASB-14). Other suitable zwitterionic detergents, depending on the embodiment, include: acetylated lecithin; apricotamidopropyl betaine; babassuamidopropyl betaine; behenyl betaine; bis 2-hydroxyethyl tallow glycinate; C12-14 alkyl dimethyl betaine; canolamidopropyl betaine; capric/caprylic amidopropyl betaine; capryloamidopropyl betaine; cetyl betaine; cocamidopropyl betaine; cocamidopropyl dimethylaminohydroxypropyl hydrolyzed collagen; N-[3-cocamido)-propyl]-N,N-dimethyl betaine, potassium salt; cocamidopropyl hydroxysultaine; cocamidopropyl sulfobetaine; cocaminobutyric acid; cocaminopropionic acid; cocoamphodipropionic acid; cocobetaine; cocodimethylammonium-3-sulfopropylbetaine; cocoiminodiglycinate; cocoiminodipropionate; coco/oleamidopropyl betaine; cocoyl sarcosinamide DEA; DEA-cocoamphodipropionate; dihydroxyethyl tallow glycinate; dimethicone propyl PG-betaine; N,N-dimethyl-N-lauric acid-amidopropyl-N-(3-sulfopropyl)-ammonium betaine; N,N-dimethyl-N-myristyl-N-(3-sulfopropyl)-ammonium betaine; N,N-dimethyl-N-palmityl-N-(3-sulfopropyl)-ammonium betaine; N,N-dimethyl-N-stearamidopropyl-N-(3-sulfopropyl)-ammonium betaine; N,N-dimethyl-N-stearyl-N-(3-sulfopropyl)-ammonium betaine; N,N-dimethyl-N-tallow-N-(3-sulfopropyl)-ammonium betaine; disodium caproamphodiacetate; disodium caproamphodipropionate; disodium capryloamphodiacetate; disodium capryloamphodipropionate; disodium cocoamphodiacetate; disodium cocoamphodipropionate; disodium isostearoamphodipropionate; disodium laureth-5 carboxyamphodiacetate; disodium lauriminodipropionate; disodium lauroamphodiacetate; disodium lauroamphodipropionate; disodium octyl b-iminodipropionate; disodium oleoamphodiacetate; disodium oleoamphodipropionate; disodium PPG-2-isodeceth-7 carboxyamphodiacetate; disodium soyamphodiacetate; disodium stearoamphodiacetate; disodium tallamphodipropionate; disodium tallowamphodiacetate; disodium tallowiminodipropionate; disodium wheatgermamphodiacetate; N,N-distearyl-N-methyl-N-(3-sulfopropyl)-ammonium betaine; erucamidopropyl hydroxysultaine; ethylhexyl dipropionate; ethyl hydroxymethyl oleyl oxazoline; ethyl PEG-15 cocamine sulfate; hydrogenated lecithin; hydrolyzed protein; isostearamidopropyl betaine; lauramidopropyl betaine; lauramidopropyl dimethyl betaine; lauraminopropionic acid; lauroamphodipropionic acid; lauroyl lysine; lauryl betaine; lauryl hydroxysultaine; lauryl sultaine; linoleamidopropyl betaine; lysolecithin; milk lipid amidopropyl betaine; myristamidopropyl betaine; octyl dipropionate; octyliminodipropionate; oleamidopropyl betaine; oleyl betaine; 4,4(5H)-oxazoledimethanol, 2-(heptadecenyl)-; palmitamidopropyl betaine; palmitamine oxide; ricinoleamidopropyl betaine; ricinoleamidopropyl betaine/IPDI copolymer; sesamidopropyl betaine; sodium C12-15 alkoxypropyl iminodipropionate; sodium caproamphoacetate; sodium caprylamphoacetate; sodium capryloamphohydroxypropyl sulfonate; sodium capryloamphopropionate; sodium carboxymethyl tallow polypropylamine; sodium cocaminopropionate; sodium cocoamphoacetate; sodium cocoamphohydroxypropyl sulfonate; sodium cocoamphopropionate; sodium dicarboxyethyl cocophosphoethyl imidazoline; sodium hydrogenated tallow dimethyl glycinate; sodium isostearoamphopropionate; sodium lauriminodipropionate; sodium lauroamphoacetate; sodium oleoamphohydroxypropylsulfonate; sodium oleoamphopropionate; sodium stearoamphoacetate; sodium tallamphopropionate; soyamidopropyl betaine; stearyl betaine; tallowamidopropyl hydroxysultaine; tallowamphopolycarboxypropionic acid; trisodium lauroampho PG-acetate phosphate chloride; undecylenamidopropyl betaine; and wheat germamidopropyl betaine.

In other embodiments, a surface active agent is preferably a non-ionic surface active agent. Examples of suitable nonionic surface active agents include, but are not limited to, polyoxyethylene (10) cetyl ether (BRIJ® 56); polyoxyethylene (20) cetyl ether (BRIJ® 58); polyoxyethyleneglycol dodecyl ether (BRIJ® 35); polyoxyethylene (9) p-t-octyl phenol (NONIDET™ P-40); polyoxyethylene (4-5) p-t-octyl phenol (TRITON™ X-45); polyoxyethylene (7-8) p-t-octyl phenol (TRITON™ X-114); polyoxyethylene (9-10) p-t-octyl phenol (TRITON™ X-100); polyoxyethylene (9-10) nonylphenol (TRITON™ N-101); polyoxyethylene (20) sorbitol monolaurate (TWEEN® 20); polyoxyethylene (20) sorbitol monopalmitate (TWEEN® 40); polyoxyethylene (20) sorbitol monooleate (TWEEN® 80); dimethyldecylphosphine oxide (APO-10); dimethyldodecylphosphine oxide (APO-12); cyclohexyl-n-ethyl-β-D-maltoside; cyclohexyl-n-hexyl-β-D-maltoside; cyclohexyl-n-methyl-β-maltoside; n-decanoylsucrose; n-decyl-β-D-glucopyranoside; n-decyl-β-maltopyranoside; n-decyl-β-D-thiomaltoside; n-dodecanoyl sucrose; decaethylene glycol monododecyl ether; N-decanoyl-N-methylglucamine; n-decyl α-D-glucopyranoside; decyl β-D-maltopyranoside; n-dodecanoyl-N-methylglucamide; n-dodecyl α-D-maltoside; n-dodecyl β-D-maltoside; heptane-1,2,3-triol; heptaethylene glycol monodecyl ether; heptaethylene glycol monododecyl ether; heptaethylene glycol monotetradecyl ether; n-hexadecyl β-D-maltoside; hexaethylene glycol monododecyl ether; hexaethylene glycol monohexadecyl ether; hexaethylene glycol monooctadecyl ether; hexaethylene glycol monotetradecyl ether; methyl-6-O-(N-heptylcarbamoyl)-α-D-glucopyranoside; nonaethylene glycol monododecyl ether; N-nonanoyl-N-methylglucamine; N-nonanoyl-N-methylglucamine; octaethylene glycol monodecyl ether; octaethylene glycol monododecyl ether; octaethylene glycol monohexadecyl ether; octaethylene glycol monooctadecyl ether; octaethylene glycol monotetradecyl ether; octyl-β-glucoside; octyl-β-thioglucoside; octyl-β-D-glucopyranoside; octyl-β-D-1-thioglucopyranoside; pentaethylene glycol monodecyl ether; pentaethylene glycol monododecyl ether; pentaethylene glycol monohexadecyl ether; pentaethylene glycol monohexyl ether; pentaethylene glycol monooctadecyl ether; pentaethylene glycol monooctyl ether; polyethylene glycol diglycidyl ether; polyethylene glycol ether; polyoxyethylene 10 tridecyl ether; polyoxyethylene (100) stearate; polyoxyethylene (20) isohexadecyl ether; polyoxyethylene (20) oleyl ether; polyoxyethylene (40) stearate; polyoxyethylene (50) stearate; polyoxyethylene (8) stearate; polyoxyethylene bis(imidazolyl carbonyl); polyoxyethylene (25) propylene glycol stearate; saponin from Quillaja bark; tetradecyl-β-D-maltoside; tetraethylene glycol monodecyl ether; tetraethylene glycol monododecyl ether; tetraethylene glycol monotetradecyl ether; triethylene glycol monodecyl ether; triethylene glycol monododecyl ether; triethylene glycol monohexadecyl ether; triethylene glycol monooctyl ether; triethylene glycol monotetradecyl ether; tyloxapol; n-undecyl β-D-glucopyranoside, (octylphenoxy)polyethoxyethanol (IGEPAL® CA-630); polyoxyethylene (5) nonylphenylether (IGEPAL® CO-520); and polyoxyethylene (150) dinonylphenyl ether (IGEPAL® DM-970). In one embodiment, a surface active agent is polyoxyethylene (5) nonylphenylether (IGEPAL® CO-520). In another embodiment, a surface active agent is polyoxyethylene (150) dinonylphenyl ether (IGEPAL® DM-970). In one embodiment, a surface active agent is preferably (octylphenoxy) polyethoxyethanol (IGEPAL® CA-630).

As will be appreciated by a skilled artisan, the amount of surface active agent added to the biological fluid can and will vary depending upon the identity of the biological fluid components in a biological fluid that may comprise a circulating miRNA. In some embodiments, the final concentration of surface active agent in the biological fluid can range from about 0.001 to about 10%. In one embodiment, the concentration of surface active agent can range from about 0.001 to about 0.01%. In another embodiment, the concentration of surface active agent can range from about 0.01% to about 0.1%. In yet another embodiment, the concentration of surface active agent can range from about 0.1% to about 1%. In another embodiment, the concentration of surface active agent can range from about 1% to about 5%. In an additional embodiment, the concentration of surface active agent can range from about 5% to about 10%.

(c) Anti-miRNA-Binding Protein Reagent

A biological fluid is contacted with an anti-miRNA-binding protein reagent. An anti-miRNA-binding protein reagent can be any agent capable of binding a miRNA-binding protein associated with circulating miRNAs. A miRNA-binding protein associated with circulating miRNAs can bind a miRNA directly, or can be indirectly associated with an RNA-protein complex comprising miRNA. Non-limiting examples of miRNA-binding proteins that can be associated with circulating miRNAs can include Argonaut, Dicer, human immunodeficiency virus (HIV) transactivating response RNA binding protein (TRBP), protein activator of the interferon induced protein kinase (PACT), the SMN complex, fragile X mental retardation protein (FMRP), Tudor staphylococcal nuclease-domain-containing protein (Tudor-SN), the putative DNA helicase MOV10, and the RNA recognition motif containing protein TNRC6B, or other components of the RISC complex or that may associate transiently or permanently with the RISC complex.

In some embodiments, a biological fluid is preferably contacted with an anti-Argonaut reagent. Non-limiting examples of an Argonaut protein can include Ago1, Ago2, Ago3, and Ago4. In one embodiment, a biological fluid is contacted with an anti-Ago1 reagent. In another embodiment, a biological fluid is contacted with an anti-Ago2 reagent. In yet another embodiment, a biological fluid is contacted with an anti-Ago3 reagent. In an additional embodiment, a biological fluid is contacted with an anti-Ago4 reagent. In another embodiment, a biological fluid is preferably contacted with a reagent capable of binding more than one Argonaut protein. For example, a biological fluid can be contacted with an anti-Ago1 and an anti-Ago2 reagent. In still another embodiment, a biological fluid is preferably contacted with a reagent capable of binding Ago1, Ago2, Ago3, and Ago4.

An anti-miRNA-binding protein reagent can be an epitope binding agent. Non-limiting examples of suitable epitope binding agents, depending upon the target molecule, include agents selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a coenzyme, a coregulator, an allosteric molecule, and an ion.

In some embodiments, an epitope binding agent is an antibody. Non-limiting examples of antibodies that can be used include polyclonal antibodies, ascites, Fab fragments, Fab' fragments, monoclonal antibodies, single chain antibodies, single domain antibodies, humanized antibodies, and other fragments that contain the epitope binding site of the antibody.

In some embodiments, a biological fluid is contacted with an anti-Argonaut antibody. In one embodiment, a biological fluid is contacted with an anti-Ago1 antibody. In another embodiment, a biological fluid is contacted with an anti-Ago2 antibody. In yet another embodiment, a biological fluid is contacted with an anti-Ago3 antibody. In another embodiment, a biological fluid is contacted with an anti-Ago4 antibody. In an additional embodiment, a biological fluid is contacted with two anti-Ago antibodies chosen from anti-Ago1, anti-Ago2, anti-Ago3, or antiAgo4 antibodies. For example, a biological fluid is contacted with anti-Ago1 and anti-Ago2 antibodies. In a further embodiment, a biological fluid is contacted with three anti-Ago antibodies chosen from anti-Ago1, anti-Ago2, anti-Ago3, or antiAgo4. In yet another embodiment, a biological fluid is contacted with all four anti-Ago antibodies. In a further embodiment, a biological fluid is contacted with an antibody capable of recognizing more than one Argonaut protein. Such antibodies may recognize one, two, three, or four Argonaut proteins. In one embodiment, a biological fluid is contacted with an anti-Argonaut antibody capable of recognizing all four human Argonaut proteins.

Contacting a biological fluid with an anti-miRNA-binding protein reagent of the disclosure forms immunoprecipitated miRNA complexes. As such, an anti-miRNA-binding protein reagent is normally attached to a solid support to form immunoprecipitated miRNA complexes when a biological fluid is contacted with the immobilized anti-miRNA-binding protein reagent. The solid support can be a material that can be modified to contain discrete individual sites appropriate for the attachment or association of an anti-miRNA-binding protein reagent. Non-limiting examples of solid support materials include glass, modified or functionalized glass, plastics including acrylics, polystyrene and copolymers of styrene and other materials, polypropylene, polyethylene, polybutylene, polyurethanes, or TeflonJ, nylon, nitrocellulose, polysaccharides, resins, silica or silica-based materials including silicon and modified silicon, carbon, metals, inorganic glasses and plastics. The size and shape of the solid support can vary without departing from the scope of the invention. A solid support can be planar, a solid support can be a well, i.e., a 364 well plate, or alternatively, a solid support can be a bead or a slide. In some embodiments, a solid support is a well of a multiwall plate. In other embodiments, a solid support is an inner surface of a pipette tip. In yet other embodiments, a solid support is preferably a bead. In some embodiments, a solid support is preferably a magnetic bead.

An anti-miRNA-binding protein reagent can be attached to a solid support in a wide variety of ways, as will be appreciated by those in the art. An anti-miRNA-binding protein reagent and a solid support can be derivatized with chemical functional groups for subsequent attachment of the two. For example, a solid support can be derivatized with a chemical functional group including, but not limited to, amino groups, carboxyl groups, oxo groups or thiol groups. Using these functional groups, an anti-miRNA-binding protein reagent can be attached using functional groups either directly, or indirectly using linkers. Alternatively, anti-miRNA-binding protein reagent can also be attached to the solid support non-covalently. For example, a biotinylated anti-miRNA-binding protein reagent can be prepared, which can bind to a solid support covalently coated with streptavidin, resulting in attachment. Additional methods of attaching an anti-miRNA-binding protein reagent to a solid support are well known in the art, and may be as described in published laboratory manuals such as in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001. In some embodiments, a biotinylated anti-miRNA-binding protein reagent is prepared, which can bind to a bead solid support covalently coated with streptavidin, resulting in attachment. As described in Section I(d) below, an anti-miRNA-binding protein reagent can be attached to a solid support before contacting a biological fluid in a method of the disclosure. Alternatively, a biological fluid of the disclosure can be contacted simultaneously with an anti-miRNA-binding protein reagent and a solid support, where the anti-miRNA-binding protein reagent attaches to the solid support. A biological fluid of the disclosure can also be contacted with an anti-miRNA-binding protein reagent before contacting the biological fluid with a solid support, where the anti-miRNA-binding protein reagent attaches to the solid support. As will be appreciated by a skilled artisan, the amount and concentration of anti-miRNA-binding protein reagent can and will vary depending upon the identity of the anti-miRNA-binding protein reagent, the volume of biological fluid used, the concentration of a miRNA in the biological fluid, and the miRNA-binding protein among other factors, and may be determined experimentally. When an anti-miRNA-binding protein reagent is a purified antibody, about 0.5 to about 10 µg of antibody can be used for each 0.2 ml plasma or serum sample.

(d) Contacting Biological Fluid and Isolating miRNA

In a method of the disclosure, a biological fluid is contacted with a surface active agent and an anti-miRNA-binding protein reagent. As will be appreciated by a skilled artisan, a biological fluid can be contacted with a variety of other agents without departing from the scope of the invention. For instance, a biological fluid can be contacted with a thiol-reducing agent to block the formation of disulfide bonds and inhibit ribonuclease activity during miRNA isolation. Suitable thiol-reducing agents include dithiothreitol (DTT), 2-mercaptoethanol, 2-mercaptoethylamine, and tris (carboxyethyl) phosphine (TCEP). A biological fluid can also be contacted with an antifoaming agent. Examples of antifoaming agents include Antifoam 204 and Antifoam O-30, Antifoam A, Antifoam B, Antifoam C, Antifoam Y-30, and Sag 471. A biological fluid can also be contacted with RNA and protein degradation inhibitors to preserve miRNA and miRNA-protein complexes.

In some embodiments a buffering agent can be used to maintain a pH suitable for isolating miRNAs. By way of non-limiting example, buffering agents may include, but are not limited to, trizma acetate, EDTA, tris, glycine, and citrate.

In some embodiments, a method of the disclosure comprises contacting a biological fluid with a surface active agent to dissociate biological fluid components before contacting the biological fluid with an anti-miRNA-binding protein reagent to form immunoprecipitated miRNA complexes. In other embodiments, a biological fluid is contacted with a surface active agent and an anti-miRNA-binding protein reagent simultaneously.

In some embodiments, an undiluted sample of biological fluid is contacted with a surface active agent and an anti-miRNA-binding protein reagent. In other embodiments, a biological fluid is diluted before contacting with a surface active agent and an anti-miRNA-binding protein reagent. Dilution of a biological fluid may be as described in section I(a) above.

Contact between a biological fluid, a surface active agent, and an anti-miRNA-binding protein reagent generally comprises a period of incubation to allow formation of immunoprecipitated miRNA complexes. A biological fluid can be contacted with a surface active agent and an anti-miRNA-binding protein reagent and incubated for about 1, 5, 10, 15, 30, 45, 60, 90, 120, 240 or 480 minutes or longer. In some embodiments, a biological fluid is contacted with a surface active agent and an anti-miRNA-binding protein reagent and incubated for about 1, 2, 3, 4, 5, 6, 7, 8, 9, 10, 11, 12, 13, 14, or about 15 minutes. In other embodiments, a biological fluid is contacted with a surface active agent and an anti-miRNA-binding protein reagent and incubated for about 10, 11, 12, 13, 14, 15, 16, 17, 18, 19, 20, 21, 22, 23, 24, 25, 26, 27, 28, 29 or about 30 minutes. In yet other embodiments, a biological fluid is contacted with a surface active agent and an anti-miRNA-binding protein reagent and incubated for about 20, 25, 30, 35, 40, 45, 50, 55, 60, 65, 70, 75, 80 85, or about 90 minutes. In other embodiments, a biological fluid is contacted with a surface active agent and an anti-miRNA-binding protein reagent and incubated for about 90, 120, 240 or 480 minutes or longer. In one embodiment, a biological fluid is preferably contacted with a surface active agent and an anti-miRNA-binding protein reagent and incubated for about 20, 25, 30, 35, 40, 45, 50, 55, or about 60 minutes.

A biological fluid can be contacted with a surface active agent and an anti-miRNA-binding protein reagent at a temperature of about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or about 30° C. or more. In some embodiments, a biological fluid is contacted with a surface active agent and an anti-miRNA-binding protein reagent at a temperature of about 0, 1, 2, 3, 4, 5, or about 6° C. In other embodiments, a biological fluid is contacted with a surface active agent and an anti-miRNA-binding protein reagent at a temperature of about 5, 6, 7, 8, 9, 10, 11, 12, 13, 14, or about 15° C. In other embodiments, a biological fluid is contacted with a surface active agent and an anti-miRNA-binding protein reagent at a temperature of about 11, 12, 13, 14, 15, 16, 17, 18, 19, 20, 21, 22, 23, 24, or about 25° C. In yet other embodiments, a biological fluid is contacted with a surface active agent and an anti-miRNA-binding protein reagent at a temperature of about 20, 21, 22, 23, 24, 25, 26, 27, 28, 29, or about 30° C.

Typically, a biological fluid is contacted with a surface active agent and an anti-miRNA-binding protein reagent under agitation. Additionally, a biological fluid can generally be removed to isolate immunoprecipitated miRNA complexes after forming the complexes, and immunoprecipitated miRNA complexes washed.

(e) Releasing miRNA

According to a method of the disclosure, miRNA is released from immunoprecipitated miRNA complexes. Methods of releasing a nucleic acid such as a miRNA from a protein complex are well known in the art and may include protease digestion, and denaturation of proteins in a nucleic acid-protein complex. In some embodiments, miRNA is released from immunoprecipitated miRNA complexes by protein denaturation. For instance, miRNA can be released from immunoprecipitated miRNA complexes by combining immunoprecipitated miRNA complexes with a guanidinium thiocyanate-phenol-chloroform solution. Released miRNA can then be purified by precipitation or using spin column chromatography.

In other embodiments, miRNA is preferably released from immunoprecipitated miRNA complexes by protease digestion. The terms "protease", "proteinase", and "peptidase" are used interchangeably herein and refer to the group of enzymes that catalyze the hydrolysis of covalent peptidic bonds. Protease enzymes are well known in the art and may include acid proteases and serine proteases. In some embodiments, a protease that can be used to release miRNA in a method of the disclosure is an acid protease. In one embodiment, an acid protease that may be used to release miRNA in a method of the disclosure is pepsin.

In other embodiments, a protease that may be used to release miRNA in a method of the disclosure is an acid protease. Six clans of serine proteases have been identified, the two largest of which are the chymotrypsin-like and the subtilisin-like clans. A large number of subtilases are known. Some of the subtilases which have been extensively studied include those obtained from various species of *Bacillus* including subtilisin DY, subtilisin Carlsberg, subtilisin BPN' (also called nagarse), mesentericopeptidase, as well as proteinase K which is obtained from Tritirachium album Limber, and thermitase which is obtained from *Thermoactinomyces vulgaris*. In certain embodiments of the present invention, proteinase K is preferred as a protease enzyme. Other protease enzymes, however, can also be used in certain embodiments, such as, for example, nagarse. The protease enzyme can thus be any of a number of proteases that produce at least a partial breakdown of proteins in immunoprecipitated miRNA complexes such that miRNA is released. In some embodiments, a protease that may be used to release miRNA in a method of the disclosure is preferably protease K.

In essence, miRNA is released from immunoprecipitated miRNA complexes by contacting complexes with a protease enzyme. As will be appreciated by a skilled artisan, the amount of protease used to release miRNA can and will vary depending on the protease, the abundance of immunoprecipitated miRNA complexes, the temperature during protease digestion, the buffer conditions used for digestion and the duration of digestion, among other factors. In general, immunoprecipitated miRNA complexes can be contacted with about 0.3 units of enzyme activity to about 30 units of enzyme activity. In certain embodiments, the amount of protease contacted with immunoprecipitated miRNA complexes can range from about 0.3 to about 1 unit, from about 1 to about 3 units, from about 3 units to about 10 units, or from about 10 units to about 30 units.

In some embodiments, using protease digestion at room temperature as described in Example 1. As used herein, the term "room temperature" is used to describe a temperature of about 10° C. to about 30° C.

Immunoprecipitated miRNA complexes can be incubated with a protease for about 0.5, 1, 2, 3, 4, 5, 6, 7, 8, 9, 10, 11, 12, 13, 14, 15, 16, 17, 18, 19 20, 25, or about 30 minutes or longer. In some embodiments, immunoprecipitated miRNA complexes are incubated with a protease for about 0.5, 1, 2, 3, 4, or about 5 minutes. In other embodiments, immunoprecipitated miRNA complexes are incubated with a protease for about 5, 6, 7, 8, 9, 10, 11, 12, 13, 14, or about 15 minutes. In yet other embodiments, immunoprecipitated miRNA complexes are incubated with a protease for about 15, 16, 17, 18, 19 20, 25, or about 30 minutes or longer.

Released miRNA may be appropriate for downstream use without further purification. Alternatively, released miRNA may be further purified for downstream uses. Methods of nucleic acid purification, such as spin column chromatography or filtration techniques, are well known in the art, e.g., according to methods described in published laboratory manuals such as in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001.

The downstream use of released miRNA may vary. Non-limiting uses of released miRNA include quantitative real-time PCR, microarray analysis, sequencing, restriction fragment length polymorphism (RFLP) analysis, single nucleotide polymorphism (SNP) analysis, microsatellite analysis, short tandem repeat (STR) analysis, and comparative genomic hybridization (CGH).

II. Kits

The invention further provides kits comprising surface active agents, anti-miRNA-binding protein reagents, and other reagents that can be used in a method of the disclosure. In some embodiments, a kit is provided for isolating miRNA from a biological fluid, which kit includes an anti-miRNA-binding protein reagent and a surface-acting agent. Anti-miRNA-binding protein reagents and surface active agents can be as described in section (I) above. In some embodiments, an anti-miRNA-binding protein reagent in a kit is an anti-Ago antibody attached to a solid support. In certain embodiments, a solid support can be a bead, a magnetic bead, or a well of a multiwall plate. In still other embodiments, a solid support can be an inner surface of a pipette tip. In some embodiments, a surface-acting agent in a kit is IGEPAL. A kit may further comprise a means for releasing miRNA from immunoprecipitated miRNA complexes. In some embodiments, a kit comprises a protease, e.g., protease K, for releasing miRNA from immunoprecipitated miRNA complexes.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As used herein, "microRNA" or "miRNA" means a small, noncoding RNA sequence of 5 to 40 nucleotides in length that can be detected in a biological specimen. Some miRNAs are derived from hairpin precursors processed, for example, by the enzyme DICER to a mature species, for example, about 18-25 nucleotides, preferably 21-23 nucleotides. MicroRNA variants are common, for example, among different animal species. In addition, variation at the 5' and 3' ends of miRNAs are common, and can be the result of imprecise cleavage by enzymes such as DICER during maturation. These variants demonstrate a scope of acceptable variation in the sequence of the miRNAs that does not impair function or the ability to detect the miRNA(s). Another type of variant is post-Dicer processing addition of non-templated nucleotide(s) to the 3' end of the miRNA (these are non-templated because they do not match the human genome). The most common variants are the miRNA sequence with an extra A or U added to the 3' end.

As used herein, the term "biological fluid" or "body fluid" can be used interchangeably and refer to a fluid isolated from a subject.

The terms "biological fluid", "biological fluid sample", or "biological sample" can be used interchangeably and refer to all biological fluids and excretions isolated from any given subject. In the context of the invention such samples include, but are not limited to, blood and fractions thereof, blood serum, blood plasma, urine, excreta, semen, seminal fluid, seminal plasma, prostatic fluid, pre-ejaculatory fluid (Cowper's fluid), pleural effusion, tears, saliva, sputum, sweat, biopsy, ascites, cerebrospinal fluid, amniotic fluid, lymph, marrow, cervical secretions, vaginal secretions, endometrial secretions, gastrointestinal secretions, bronchial secretions, breast secretions, ovarian cyst secretions, and tissue fluid samples.

An "isolated" polynucleotide is a nucleic acid molecule that is identified and separated from at least one contaminant with which it is ordinarily associated in its natural source. An isolated nucleic acid molecule is other than in the form or setting in which it is found in nature. Isolated nucleic acid molecules therefore are distinguished from the specific nucleic acid molecule as it exists in natural cells.

As various changes could be made in the above-described animals, cells and methods without departing from the scope of the invention, it is intended that all matter contained in the above description and in the examples given below, shall be interpreted as illustrative and not in a limiting sense.

EXAMPLES

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1: General miRNA Isolation Protocol

A representative protocol used to isolate circulating miRNAs comprises performing RNA immunoprecipitation (RIP) in the presence of a detergent to release vesicle-associated miRNAs. In this protocol, miRNAs are separated from other cellular components such as other RNAs, plasma proteins, etc. without the use of phenol, chaotropes, or column purification, and may be completed in 40-70 minutes.

The protocol consists of three steps:
1) Plasma components are treated with a detergent,
2) miRNA/protein complexes are immunoprecipitated, and
3) miRNA is released from immunoprecipitated miRNA complexes.

Protein A (Sigma-Aldrich GE28-9670-56), Protein G (Sigma-Aldrich GE28-9670-66), or Streptavidin (Sigma-Aldrich GE28-9857-38) beads were coated with anti-Ago antibody by transferring 20 µl of magnetic beads (10% slurry) to 0.1 ml RIP wash buffer (50 mM Tris-HCl, pH 7.4, 0.05% IGEPAL® CA-630), washing the beads with RIP wash buffer once, and using a magnetic stand for separating the beads from the solution. The washed magnetic beads were then resuspended in 0.1 ml RIP wash buffer before adding 2.5-10 µg unbiotinylated or biotinylated anti-Ago (Sigma-Aldrich SAB4800048), anti-Ago2 (Sigma-Aldrich SAB4200085), or anti-Ago1 (Sigma-Aldrich SAB4200084) antibody. The beads and antibody were incubated with rotation at room temperature for about 30 minutes. The beads were then separated from the solution using a magnetic stand. The antibody beads were then washed twice with 0.5 ml RIP wash buffer.

In the first step of the miRNA isolation process, 0.2 ml plasma, 8 µl 25% IGEPAL CA-630 (Sigma-Aldrich I8896; 40 µl 25% IGEPAL per ml plasma to produce a final concentration of 1%), 2 µl protease inhibitor cocktail (PIC; Sigma-Aldrich P8340; 10 µl/ml plasma), and 0.8 µl RNase inhibitor (Sigma-Aldrich R1158; 4 µl/ml plasma) were added to the prepared Ago antibody beads. Alternatively, plasma may be treated with detergent and inhibitors while preparing beads, and pre-treated plasma added subsequently to the antibody beads.

In the second step, miRNA/protein complexes were immunoprecipitated by incubating the sample at room temperature for 1 hr or 4° C. overnight with rotation. The beads were washed 5× with 1 ml wash RIP buffer, and collected using the magnetic stand to separate the beads from the supernatant. The beads can be centrifuged briefly and returned to the magnetic stand to remove residual supernatant.

In the third step, precipitated miRNA associated with antibody beads was released from the protein complex and the beads by extraction with TRI Reagent®BD or QIAzol lysis reagent followed by isopropanol precipitation with ammonium acetate and linear acrylamide, as described in the Technical Bulletin for Sigma-Aldrich Imprint RNA Immunoprecipitation Kit (RIP), or purified with Qiagen's miRNeasy Serum/Plasma Kit. Alternatively, and preferably, miRNA was released by proteinase K digestion. Twenty µl proteinase K mix (14 µl water, 2 µl 10× proteinase K release buffer, and 4 µl P4850 proteinase K) was added to the beads from step two, and incubated at room temperature for 10 minutes on vortex genie 2, setting 4. The 10× proteinase K release buffer comprises 100 mM Tris, pH 8.0, 15 mM $MgCl_2$, 500 mM KCl, 100 mM DTT, and 1% IGEPAL. Immediately after incubation, the beads were removed by placing on a magnetic stand and transferring the supernatant comprising free miRNA to a fresh tube. Proteinase K in the supernatant was then inactivated by incubating the sample at 95° C. for 5 minutes. Specific miRNAs were detected with Sigma-Aldrich's MystiCq RT-qPCR assays using 5 µl of each miRNA preparation per 10 µl polyA-tailing reaction. Synthetic miRNAs, i.e., single-stranded RNA with the same sequence as mature miRNAs listed in miRBase, were diluted in 0.02 mg/ml linear acrylamide to known copy number based on absorbance of stock solutions at 260 nm, assayed in parallel with miRNAs prepared from plasma, and used as standards for absolute quantitation.

Example 2: Immunoprecipitation of miRNAs from Plasma is More Efficient Than Tri Reagent Alone The efficiency of miRNA isolation from plasma using RNA immunoprecipitation (RIP) was compared to miRNA isolation using TRI Reagent®BD (Sigma-Aldrich). TRI Reagent®BD is a reagent for use in the simultaneous isolation of RNA, DNA and protein from blood derivatives such as serum, plasma or whole blood.

Isolation of miRNA using TRI Reagent®BD was according to the manufacturer's instructions. In short, 0.2 ml plasma was mixed with TRI Reagent®BD, and miRNA was extracted using chloroform for phase separation before isopropanol precipitation in the presence of ammonium acetate and linear acrylamide, and washing of RNA for analysis. Isolation of miRNAs using RIP was performed with 2.5 µg anti-Ago2 antibody bound to 20 µl Protein A magnetic beads. miRNA was recovered from the beads by extraction with TRI Reagent®BD and isopropanol precipitation in the presence of ammonium acetate and linear acrylamide, as for the direct plasma extraction.

The level of let-7a-5p, miR23a-3p, miR191-5p, miR142-3p, and miR451a miRNAs in the prepared samples was determined by quantitative, real-time RT-PCR. RIP of miRNA from plasma was about 5 to about 600 fold more efficient than TRI Reagent®BD (FIG. 1).

Example 3. RIP Yield Similar to Yield From a Commercial Kit

The efficiency of miRNA isolation from plasma using RNA immunoprecipitation (RIP) was compared to miRNA isolation using Qiagen's miRNeasy Serum/Plasma Kit (Qiagen). Qiagen miRNeasy employs spin columns comprising silica resin that selectively binds DNA or RNA, and is recommended for miRNA isolation from ≤0.2 ml serum or plasma.

Isolation of miRNA using Qiagen miRNeasy Serum/Plasma Kit was according to the manufacturer's instructions. In short, 0.2 ml plasma was mixed with QIAzol reagent, and miRNA was purified from the aqueous layer using the provided spin columns. Isolation of miRNAs using RIP was performed with 20 µl Protein A magnetic beads to which 2.5 µg anti-Ago2 antibody was bound. miRNAs were released from the beads with QIAzol reagent and purified with the Qiagen kit, as for the direct plasma extraction.

Figure 2:
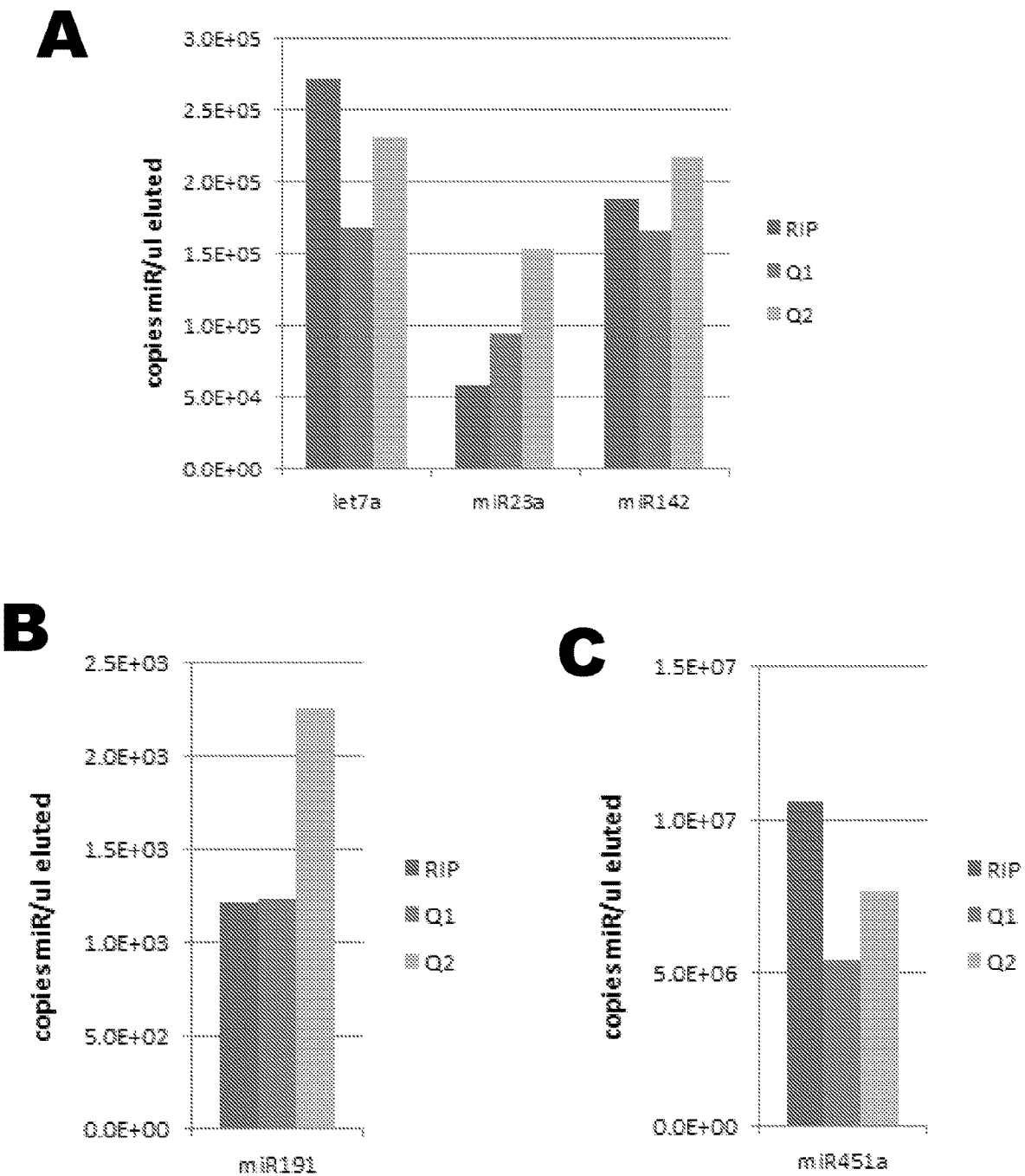
FIG. 2 presents three plots showing levels of miRNAs isolated from plasma using Ago-RIP or a Qiagen column purification kit (Q1, Q2). The amounts of isolated miRNA, as copies of miR/μl eluted, are shown for let-7a, 23a, and 142 miRNAs (A), 191 miRNA (B), and 451a miRNA (C).

The level of let-7a, miR23a, miR191, miR142, and miR451a miRNAs in the prepared samples was determined by quantitative, real-time RT-PCR. Yield of miRNAs using RIP was similar to miRNA yield using the Qiagen kit alone (FIG. 2).

Figure 3:
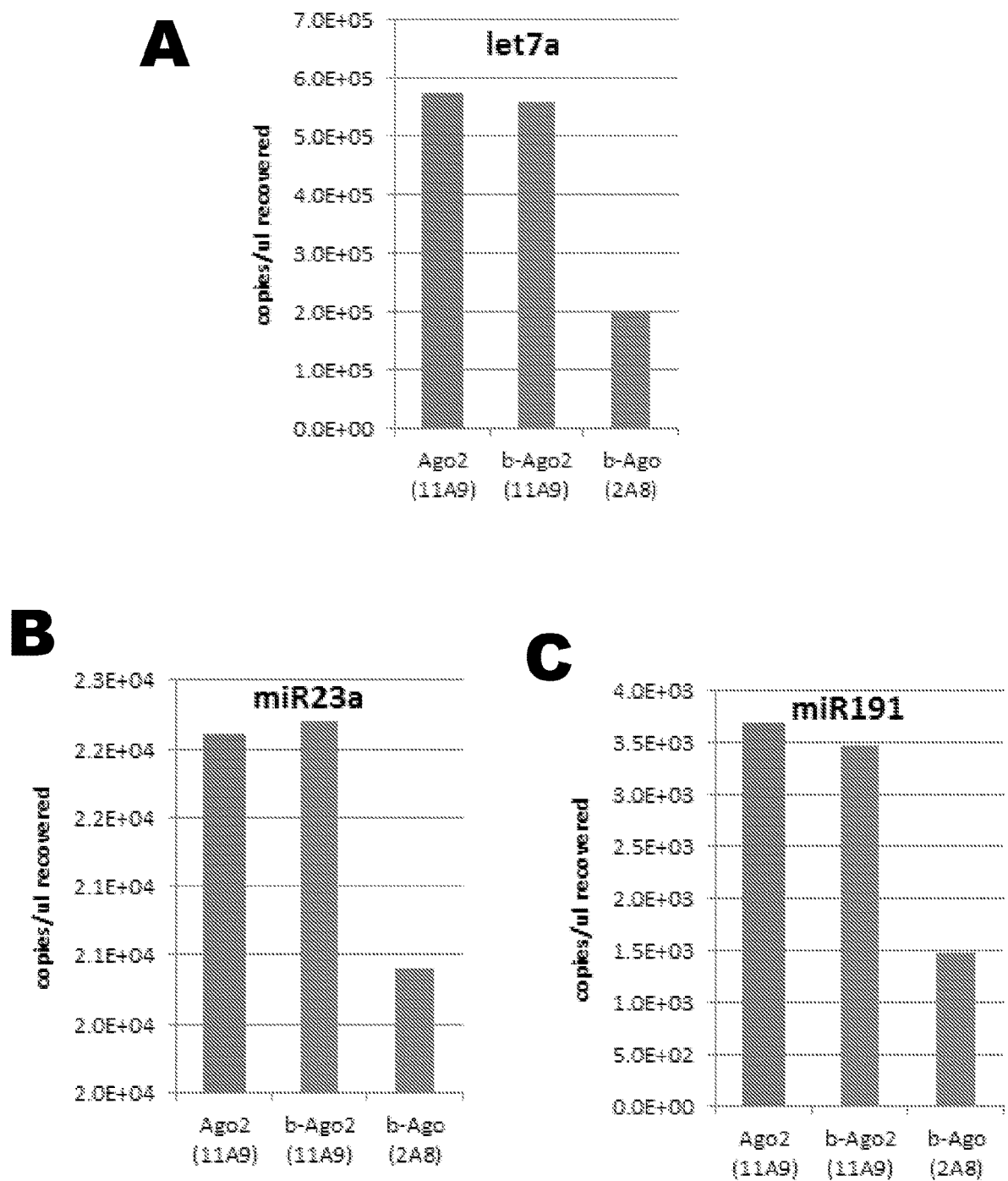
FIG. 3 presents three plots showing levels of miRNAs isolated from plasma using RIP with biotinylated (b-Ago2 or b-Ago) or non-biotinylated (Ago2) antibodies with streptavidin or Protein A beads. Shown are the amounts of isolated miRNA represented as copies of miR/μl eluted for let-7a (A), 23a (B), and 191 (C) miRNAs. The antibody (clone in parenthesis) used is noted on the x axes.

Example 4. Comparing RIP Using Biotinylated and Non-Biotinylated Anti-Ago Antibody and Streptavidin Beads Protein A and Protein G beads both bind human IgG, which is extremely abundant in plasma. To avoid co-isolating IgG, anti-Ago (clone 2A8) and anti-Ago2 (clone 11A9) antibodies were biotinylated with Pierce EZ-Link Sulfo-NHS-LC-LC-Biotin (Thermo Scientific) for RIP with streptavidin beads. Ago-RIP was performed using 2.5 µg of the biotinylated anti-Ago2 (b-Ago2) or anti-Ago (b-Ago) antibody and 20 µl streptavidin magnetic beads, or with 2.5 µg of non-biotinylated anti-Ago2 antibody and 20 µl Protein A beads. RIP with biotinylated anti-Ago2 (b-Ago2) antibody and streptavidin beads gave the same yield of miRNAs as RIP with anti-Ago2 antibody with Protein A beads (see FIG. 3). RIP with biotinylated anti-Ago gave significantly lower miRNA yields, as they had with unbiotinylated anti-Ago and Protein A beads.

Example 5. Heat Release of miRNA Isolated Using RIP Negatively Affects Yield

Heating in nuclease-free water was tested as a means to release miRNAs following RIP. Ago-RIP was performed with 0.2 ml plasma and 2.5 µg of either unbiotinylated anti-Ago or anti-Ago2 antibody on Protein A magnetic beads, or biotinylated anti-Ago or anti-Ago2 antibody on streptavidin magnetic beads. Fourteen µl of nuclease-free water was added to the beads, and these mixtures were heated at 40°, 50°, or 60° C. for 2 minutes before removing the beads. RIP followed by heat release was compared with RIP followed by miRNA purification with Qiagen miRNeasy Serum/Plasma Kit, and miRNAs purified directly from plasma with the Qiagen kit. Synthetic cel-miR-39-3p (1.4e8 copies) was spiked in after QIAzol addition for Qiagen preps or in the water added to post-RIP beads.

Figure 4:
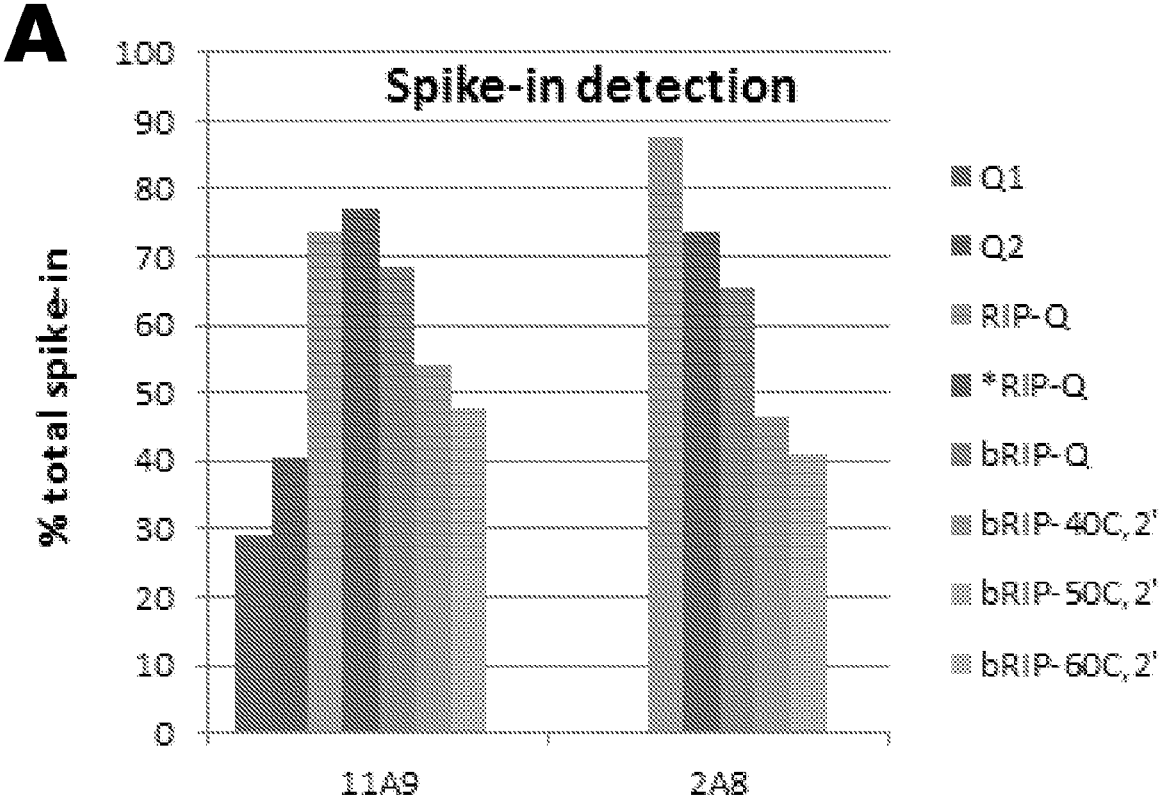
FIG. 4 presents two plots showing levels of miRNAs isolated from plasma using Ago-RIP with heat release. Q represents Qiagen column purification; RIP-Q represents immunoprecipitation followed by Qiagen column purification; bRIP-Q represents immunoprecipitation using biotinylated antibody followed by Qiagen column purification. (A) depicts levels of synthetic cel-miR-39-3p spike-in using Qiagen column purification, RIP in combination with column purification and RIP with protease K release. Levels of spike-in are represented as percent total of synthetic cel-miR-39-3p spiked-in during isolation. (B) depicts levels of let7a miRNA isolated from plasma using Qiagen column purification, RIP in combination with column purification and RIP with protease K release. Levels of let7a are represented as copies of let7a in 1 μl of recovered sample.
Figure 4:
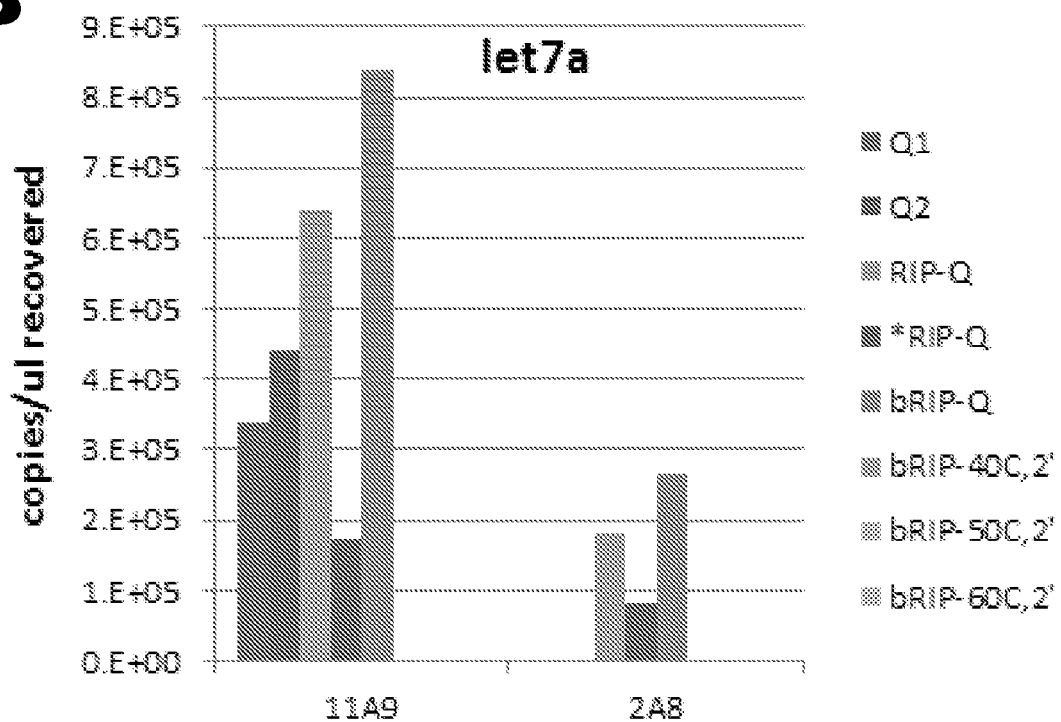

Synthetic cel-miR-39-3p spike-in was undetected after 2 minutes at 60° C. with RIP product on beads (FIG. 4). There was also no endogenous miRNA detected after 2 minutes at 40°, 50° or 60° C. Similar results were observed for miR23a, miR142, miR191, and miR451a. Let7a miRNA was also lost when samples were heated to 50° or 60° C. The loss of miRNA is likely due to RNase carry-over contamination with RIP, since blood is known to contain extremely high levels of RNase.

Example 6. Release of miRNA Using Proteinase K Digestion

Proteinase K digestion was tested as a means to release miRNA after Ago-RIP. RIP was performed with 0.2 ml plasma and 2.5 µg of biotinylated anti-Ago2 antibody bound to 20 µl streptavidin magnetic beads. Post-RIP, beads were incubated in digestion buffer (20 µl of 10 mM Tris-HCL, pH 8.0, 1.5 mM $MgCl_2$, 50 mM KCl, 10 mM DTT, 0.1% IGEPAL) containing 4 µl proteinase K (Sigma-Aldrich P4850) at room temperature or 37° C. for 10 minutes with agitation, or at 65° C. for 2 minutes with agitation. After removing the beads, Proteinase K was inactivated at 95° C. for 5 minutes and 5 µl of each proteinase K digest was added to a 10 µl polyA-tailing reaction for specific miRNA detection with Sigma-Aldrich's MystiCq RT-qPCR assays. For comparison, a parallel preparation of post-RIP beads were extracted with QIAzol lysis reagent and purified with miRNeasy Serum/Plasma ("total", set at 100%). miRNA levels from RIP-proteinase K were expressed relative to those from RIP in which miRNAs were released using the miRNeasy kit.

Figure 5:
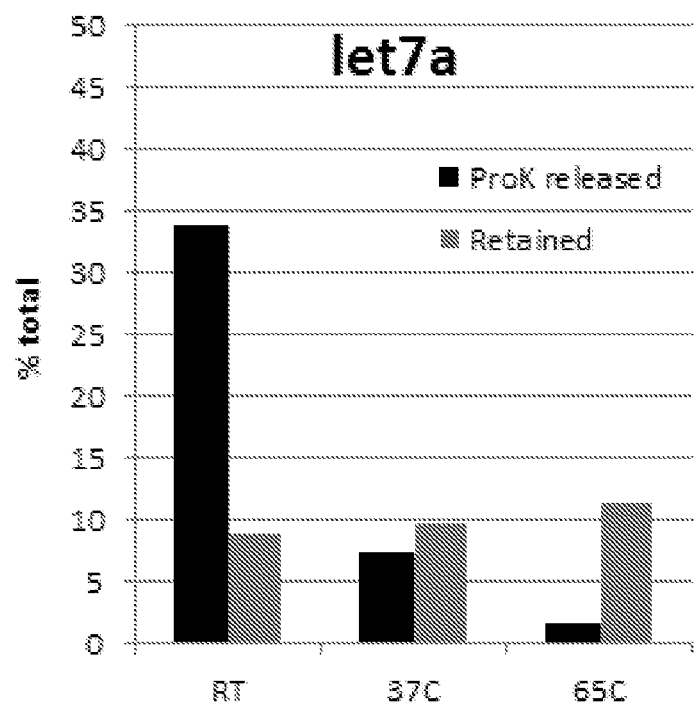
FIG. 5 presents two plots showing levels of miRNAs isolated from plasma using Ago-RIP with protease K release at various temperatures. (A) depicts levels of let7a miRNA released by protease K (left bar at each temperature), and levels retained on the beads (right bar at each temperature). Levels of let7a miRNA are represented as percent total of let7a miRNA in 0.2 ml of the same plasma isolated with Qiagen's miRNeasy Serum/Plasma Kit. (B) depicts levels of miR451a miRNA released by protease K (left bar at each temperature), and levels retained on the beads (right bar at each temperature). Levels of miR451a miRNA are represented as percent total of miR451a miRNA in 0.2 ml of the same plasma isolated with Qiagen's miRNeasy Serum/Plasma Kit.
Figure 5:
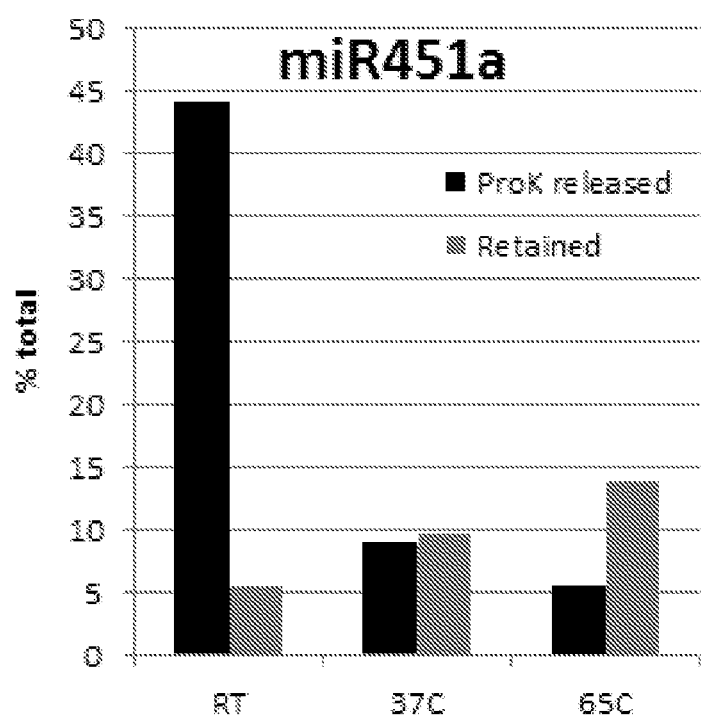

Release of miRNA using proteinase K digestion at room temperature yielded more miRNAs than release at higher temperatures (FIG. 5). In all cases, a significant amount of total miRNA was lost. The loss was most likely due to residual RNAse in the sample.

A similar experiment was performed using pepsin digestion in buffers at pH 2, 3, or 4 for release of miRNA instead of proteinase K. miRNA release using pepsin recovered less than 1% of miRNA (data not shown).

Figure 6:
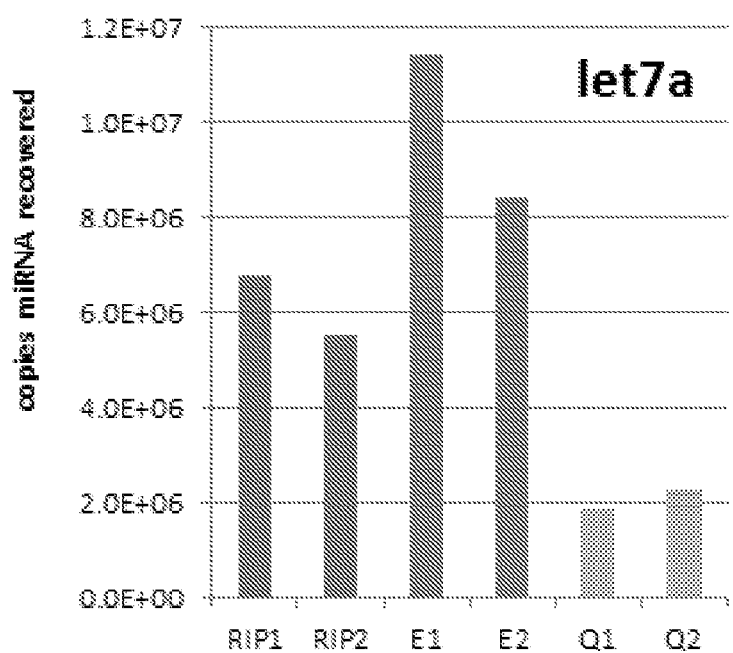
FIG. 6 presents two plots showing levels of let7a (A) or miR451a (B) miRNA isolated from plasma using commercially available methods of miRNA isolation, or isolation using RIP with protease K release in standard tubes. E1 and E2 represent miRNA isolation using miRCury RNA Isolation Kit-biofluids from Exiqon. Q1 and Q2 represent miRNA isolation using miRNeasy Serum/Plasma Kit from Qiagen. RIP-std-Q represents immunoprecipitation followed by Qiagen column purification. Levels of miRNA are represented as total copies recovered from 0.2 ml plasma.
Figure 6:
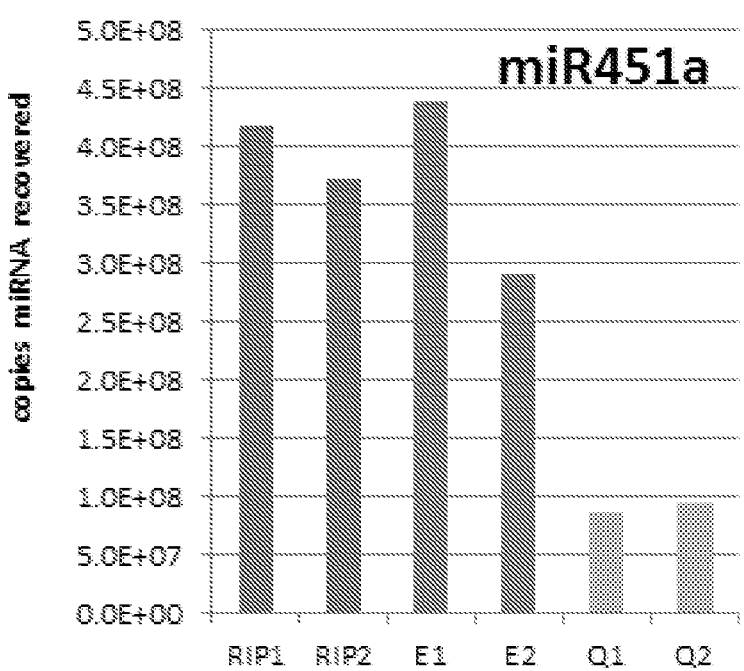
Figure 7:
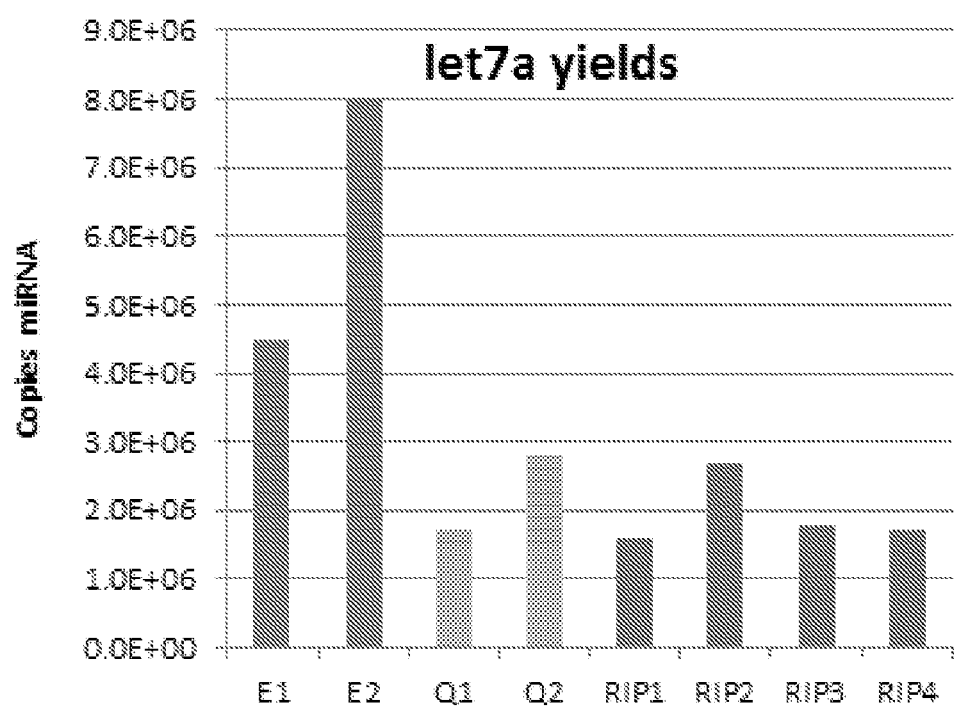
FIG. 7 presents two plots showing levels of let7a miRNA isolated from plasma using commercially available methods of miRNA isolation, or isolation using Ago-RIP with protease K release (RIP1-4). (A) Shows trial 1 and (B) shows trial 2. E1 and E2 represent miRNA isolation using miRCury RNA Isolation Kit—Biofluids from Exiqon. Q1 and Q2 represent miRNA isolation using miRNeasy Serum/Plasma Kit from Qiagen. Levels of let7a are represented as total copies of let7a recovered from 0.2 ml plasma.
Figure 7:
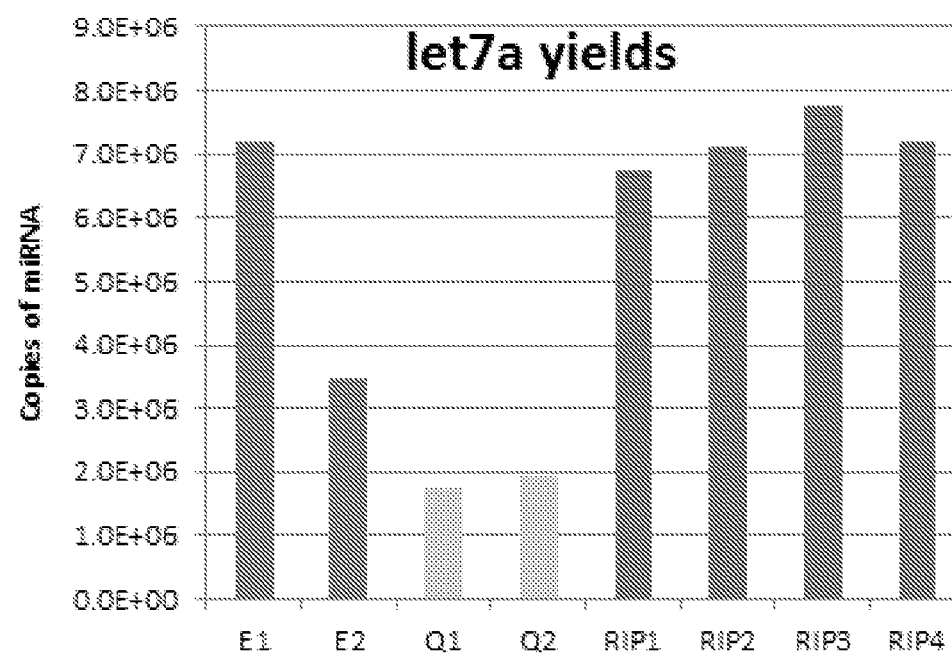

Example 7. Comparing RIP with Other Methods for miRNA Extraction from Biofluids miRNAs were isolated using biotinylated anti-Ago2 and streptavidin magnetic beads and protease K release essentially as described in Example 6. For comparison, miRNAs was also purified directly from plasma using the miRCury™ RNA Isolation Kit—Biofluids from Exiqon, or the miRneasy Serum/Plasma Kit from Qiagen (FIG. 6). These data show that let7a miRNA yields from RNA purified using Exiqon's kit were 3-4 times higher than that purified using Qiagen's kit. Yields of most miRNAs prepared using Ago-RIP and proteinase K release were intermediate between those of Exiqon and Qiagen in most experiments. Results for let7a are shown in FIG. 6 and FIG. 7, but those for miR23a, miR142, and miR191 were similar. On the other hand, yields of miR451a were similar for Ago-RIP and Exiqon. miR451a requires Ago2 slicer activity for processing to a mature miRNA, and therefore, only occurs in Ago2 complexes. Other miRNAs can associate with Ago1, Ago3, or Ago4 in addition to Ago2. Since the antibody used is specific for Ago2, it isolates miR451a more efficiently than it does all other mature miRNAs.

Example 8. RIP with or Without Protease Inhibitors and RNAse Inhibitors

Figure 8:
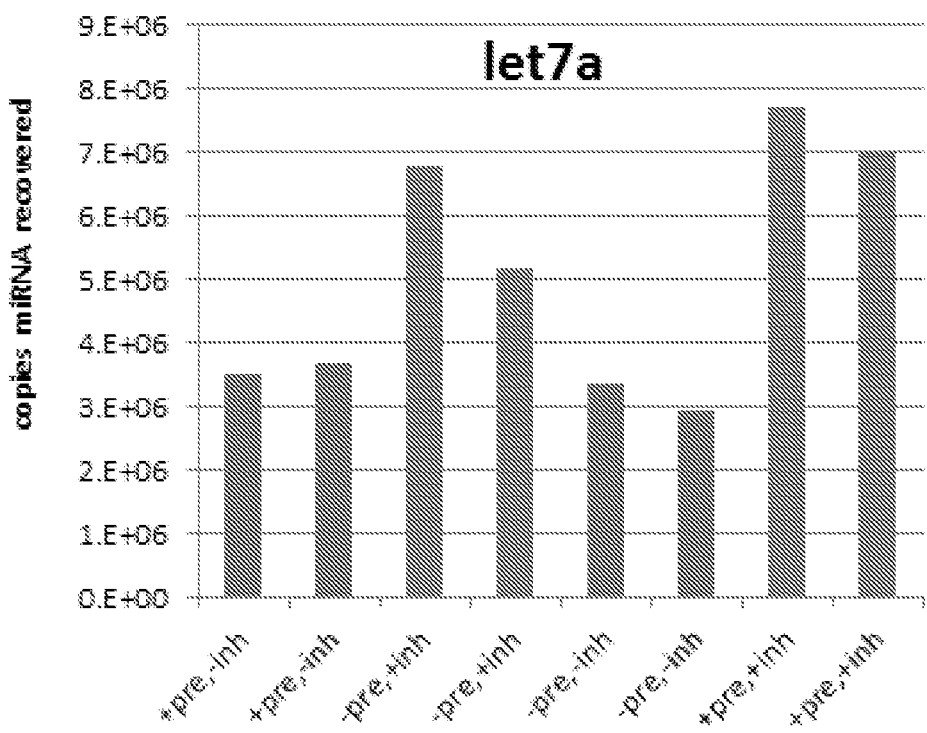
FIG. 8 presents two plots showing levels of miRNAs isolated from plasma using Ago-RIP followed by protease K release with or without protease and RNase inhibitors, and with or without detergent pretreatment. +pre,+inh; Igepal and inhibitors added to plasma and incubated ~30 minutes before adding to Ago2-beads. +pre,−inh; Igepal added to plasma without inhibitors and incubated ~30 minutes before adding to Ago2-beads. −pre,+inh; Igepal and inhibitors added to plasma at the same time as Ago2-beads. −pre,−inh; Igepal added to plasma without inhibitors at the same time as Ago2-beads. (A) Depicts copies of let7a miRNA recovered, and (B) depicts copies of miR451a miRNA recovered.
Figure 8:
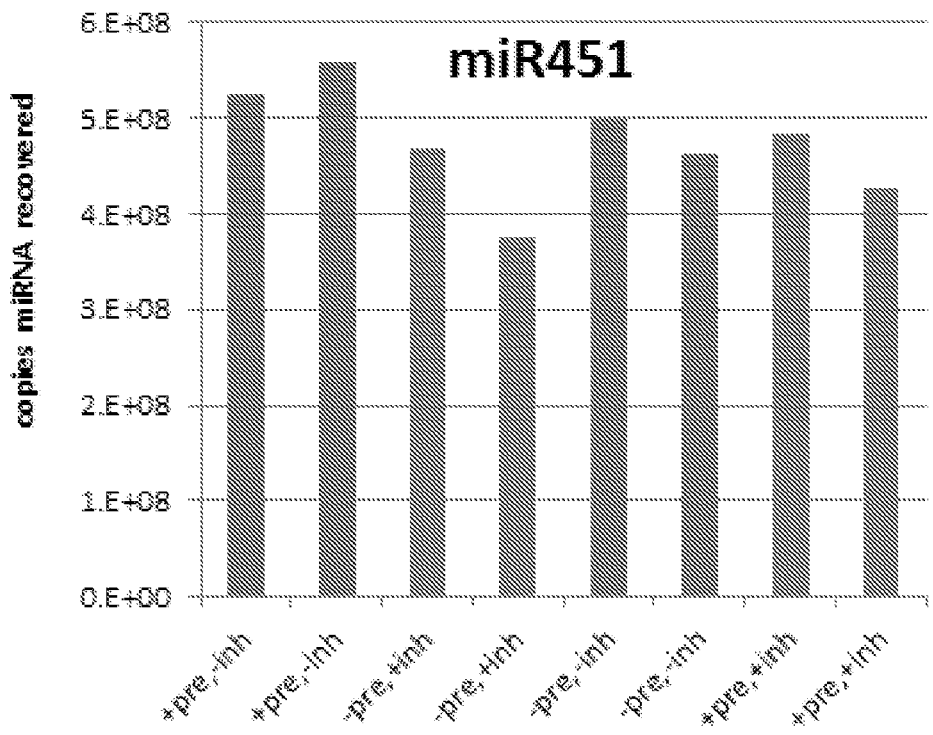

Ago-RIP was used to isolate miRNAs in the presence (+inh) or absence (−inh) of protease inhibitors and RNase inhibitors, and miRNAs were released from the beads with protease K. Ago-RIP performed in the presence of inhibitors yielded more let7a miRNA than samples that were not treated with inhibitors. Similar results were found for miR191. There was no significant difference for miR451a (FIG. 8).

Pretreatment of serum with IGEPAL with or without inhibitors was also performed (+pre), and compared to addition of IGEPAL with or without inhibitors at the same time as addition of antibody beads (−pre). The results show that pretreatment of serum with protease and RNAse inhibitors did not improve yields of either let7a or miR451a when compared to co-treatment (FIG. 8).

Example 9. miRNA Recovery with or Without Detergent

Figure 9:
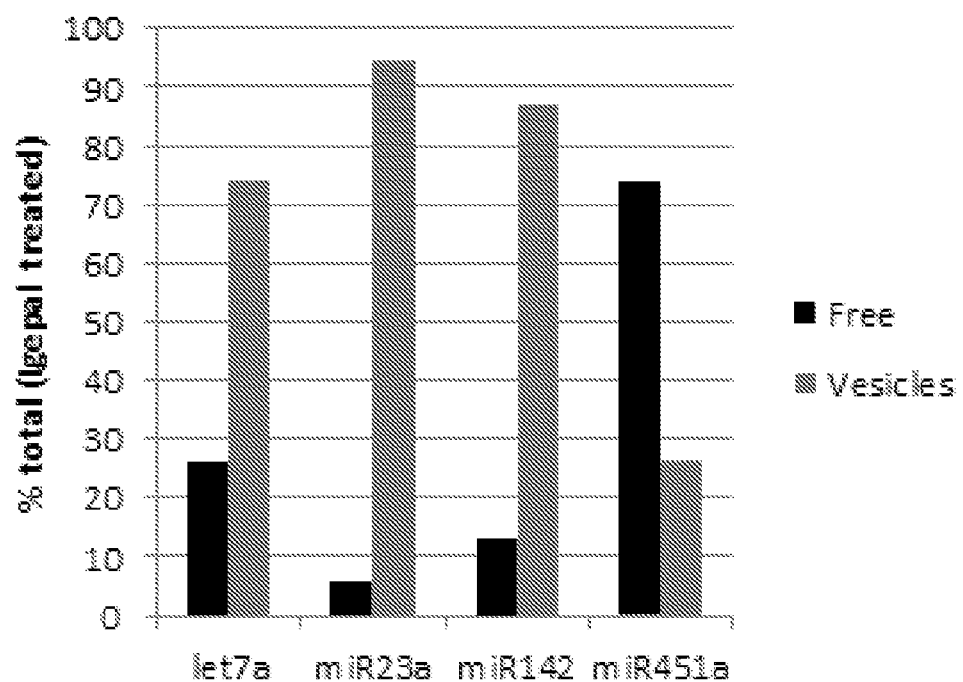
FIG. 9 presents a plot showing the levels of free (left bar for each miRNA) and vesicular (right bar for each miRNA) for the indicated miRNAs as % total IGEPAL treated miRNAs.

To determine the effect of detergent on the isolation of miRNAs, Ago-RIP was performed (with 0.2 ml plasma) in the presence or absence of IGEPAL detergent using 10 µg of biotinylated anti-Ago2 antibody/streptavidin magnetic beads. It was assumed that any miRNA isolated in the absence of detergent was free (i.e., not in a vesicle), and any isolated in the presence of detergent was vesicular. Total miRNA was the level of a miRNA recovered from IGEPAL-treated plasma, and was set to 100%. Free miRNA (miRNA not associated with vesicles) was the level of a miRNA recovered from plasma that was not treated with IGEPAL. Vesicle-associated miRNA was calculated as the level of a miRNA in the total miRNA sample subtracted by the level of said miRNA in the free miRNA sample. FIG. 9 shows the free and vesicle-associated levels of let7a, miR23a, miR142, and miR451a miRNAs. These results show that detergent treatment may be desirable to recover some miRNAs efficiently from plasma by RIP.

Example 10. RIP is Scalable

Figure 10:
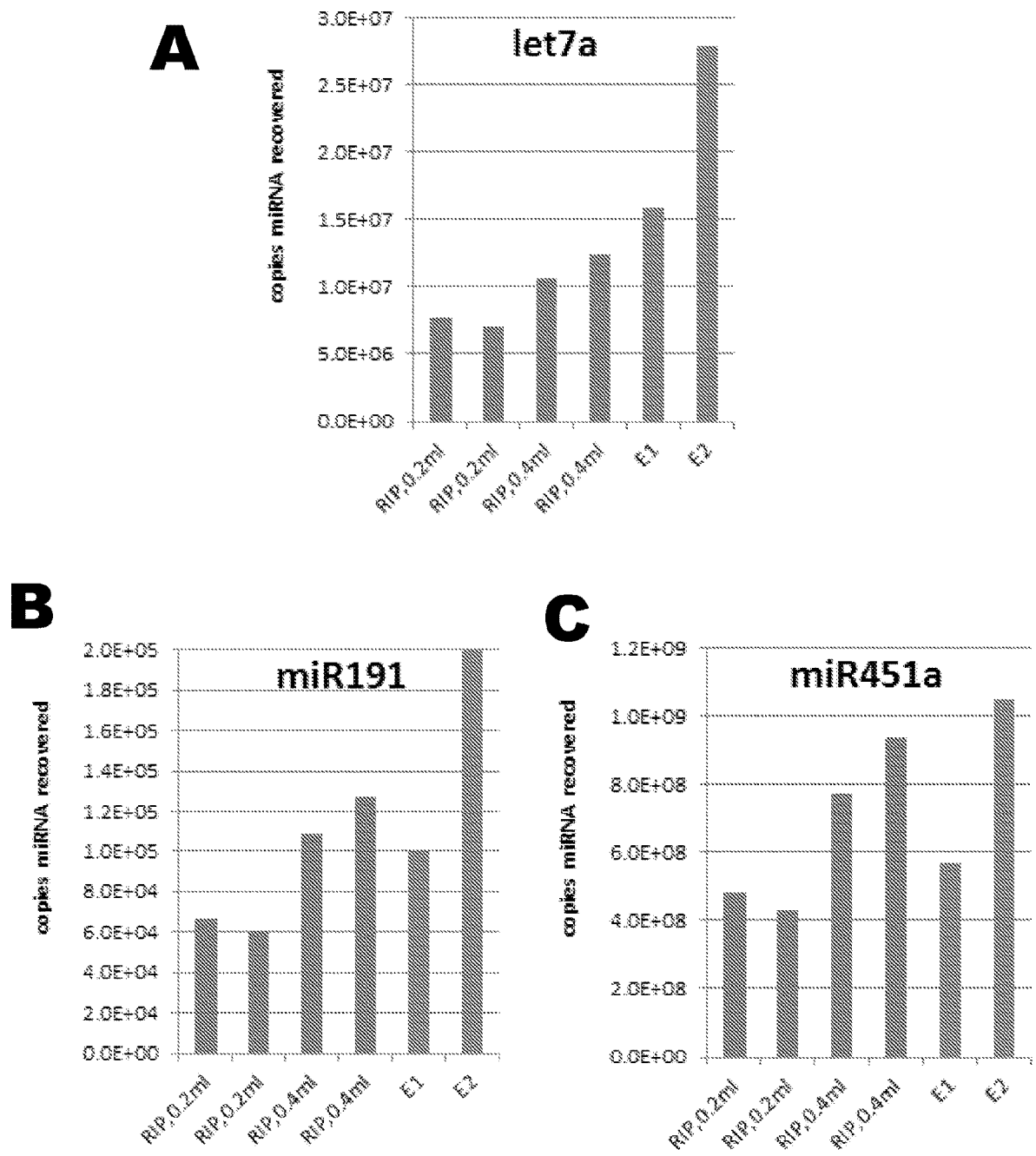
FIG. 10 presents three plots showing levels of miRNAs isolated from 0.2 or 0.4 ml plasma using Ago-RIP followed by protease K release (RIP), or from 0.2 ml plasma using miRCury RNA Isolation Kit-Biofluids from Exiqon (E). (A) Depicts copies of let7a miRNA recovered, (B) depicts copies of miR191 miRNA recovered, and (C) depicts copies of miR451a miRNA recovered.

RIP was performed with 0.2 ml plasma and 10 µg biotinylated anti-Ago2/streptavidin beads, or 0.4 ml plasma and 20 µg biotinylated anti-Ago2/streptavidin beads, followed by release with proteinase K digestion. For comparison, miRNAs were isolated from 0.2 ml of the same plasma with Exiqon's miRCury RNA Isolation Kit—Biofluids. Total yields of let7a, miR191, and miR451a recovered with each preparation method are shown in FIG. 10. With Ago-RIP, twice as much plasma (i.e., 0.4 ml versus 0.2 ml) yielded 1.5-2-times as much of the miRNAs tested, whereas column-based kits (such as those from Exiqon and Qiagen) are capacity-limited and recommend the use of no more than 0.2 ml of plasma.

Example 11. Minimum Incubation and Washing Times for RIP

Figure 11:
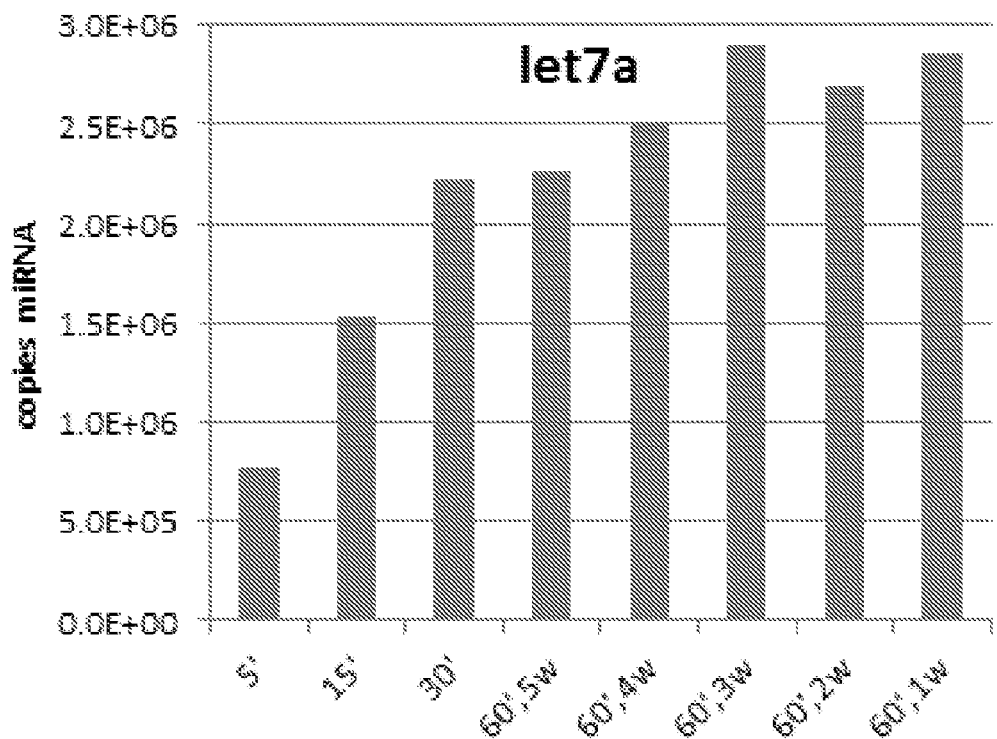
FIG. 11 presents a plot showing the levels of let7a isolated from plasma using Ago-RIP followed by protease K release. RIP incubations were at room temperature for 5, 15, 30, or 60 minutes (5', 15', 30', 60'). Those incubated 5, 15, or 30 minutes were all washed 5 times before proteinase K release. Those incubated 60 minutes were washed 5, 4, 3, 2, or 1 times (5w, 4w, 3w, 2w, 1w). Total yield of let7a recovered from 0.2 ml plasma is shown.

RIP was performed with 0.2 ml plasma and 5 µg biotinylated anti-Ago2/streptavidin beads, incubated with rotation at room temperature for 5, 15, 30, or 60 minutes. Those incubated for 5, 15, or 30 min were all washed 5 times after the incubation was completed. Those with 60 min incubations were washed 5, 4, 3, 2, or 1 times with the RIP wash buffer. All were released with proteinase K. Yields for let7a are presented in FIG. 11. The results show that an incubation period of more than 15 minutes appears to be needed for maximum miRNA recovery under the conditions used (e.g., type and amounts of antibody and beads), but only one wash is needed before miRNA detection with Sigma-Aldrich's MystiCq assays (polyA tailing, RT, qPCR). Similar results were obtained for miR122, miR191, and miR451a.

Example 12. RIP is Specific for miRNAs

The following example was performed to determine whether Ago-RIP is specific for miRNAs or whether Ago-RIP also isolates other RNAs. Isolations were performed using Ago-RIP (S), Exiqon's miRCury RNA Isolation Kit—Biofluids (E), or Qiagen's miRneasy Serum/Plasma Kit (Q) from 0.2 ml fresh plasma (experiments 1 and 2) or 0.2 ml frozen plasma (experiment 3). Experiment 1 was performed with 2.5 µg biotinylated anti-ago2 antibody/20 µl streptavidin beads. Experiments 2 and 3 were performed with 2.5 µg biotinylated anti-ago2 antibody/20 µl streptavidin beads. Proteinase K digestion essentially as described above in Example 6 was used to release the miRNAs from the beads. Specific miRNAs (e.g., let7a) and specific small nuclear or nucleolar RNAs (e.g., RNU6 or SNORD48) were detected using MystiCq RT-qPCR assays, and longer mRNAs or rRNAs (e.g., GAPDH, RN18S, RN28S) were detected using KiCqStart® RT-qPCR (Sigma-Aldrich) assays. Total RNA from HeLa cells (isolated using TRI Reagent®BD) was used for quantitation standards.

Figure 12A:
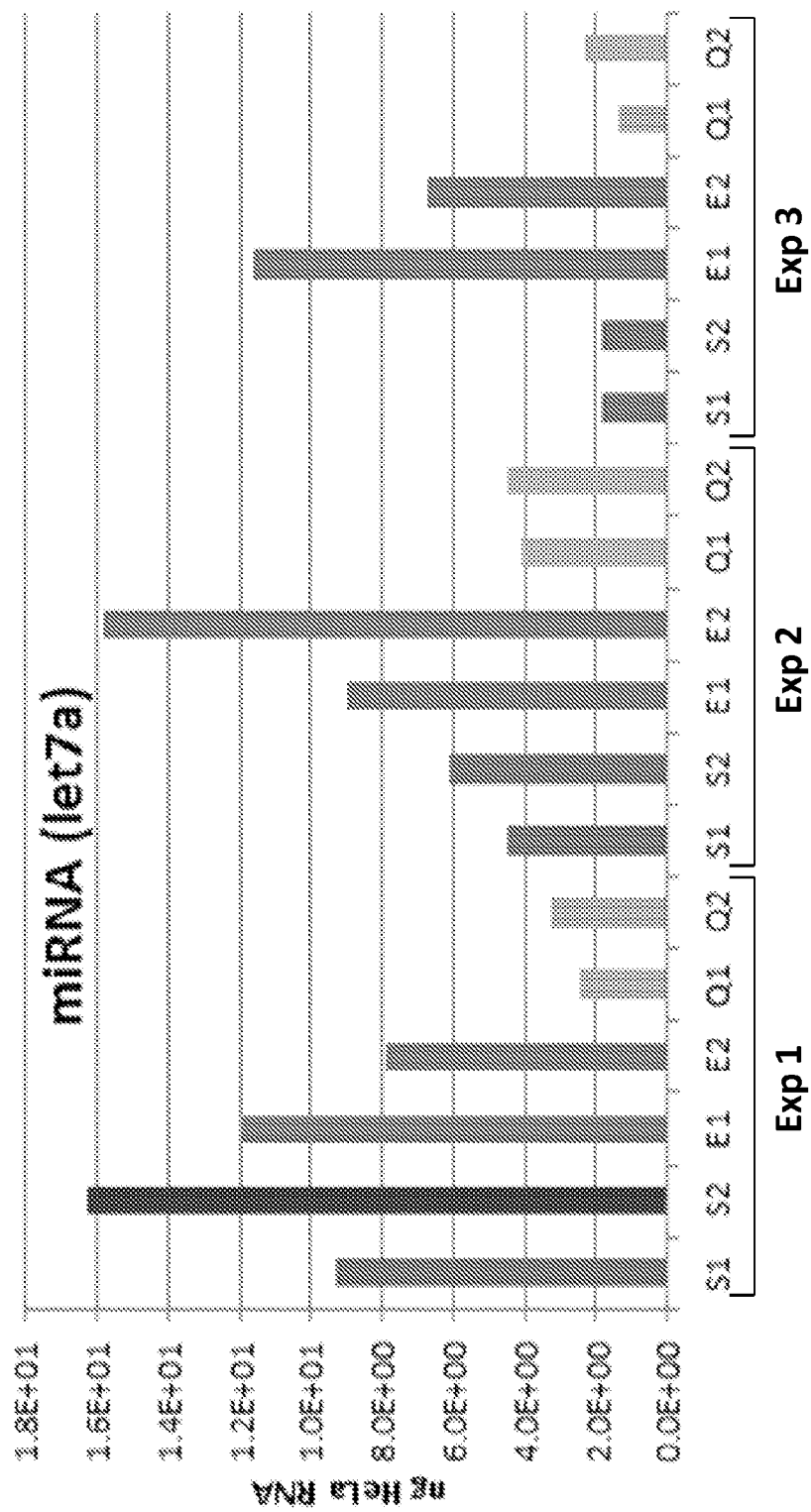
FIG. 12A shows the levels of let7a miRNA isolated from plasma using Ago-RIP or column-based miRNA isolation kits. Three different experiments (Exp) are presented. S1 and S2 represent isolation using Ago-RIP; E1 and E2 represent isolation using miRCury RNA Isolation Kit-Biofluids from Exiqon; and Q1 and Q2 represents isolation using miRNeasy Serum/Plasma Kit from Qiagen.
Figure 12B:
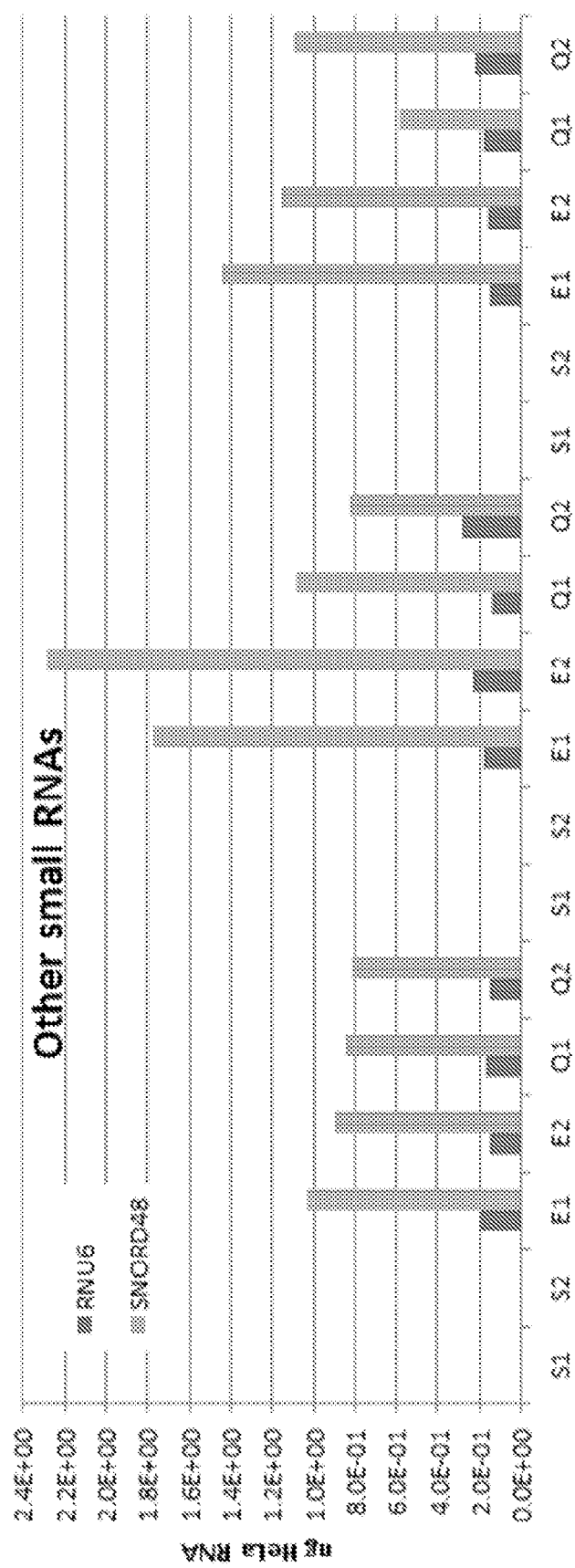
FIG. 12B presents the levels of RNU6 small nuclear RNA and SNORD48 small nucleolar RNA isolated from plasma using Ago-RIP or column-based miRNA isolation kits. Three different experiments are presented. S1 and S2 represent isolation using Ago-RIP; E1 and E2 represent isolation using miRCury RNA Isolation Kit-Biofluids from Exiqon; and Q1 and Q2 represents isolation using miRNeasy Serum/Plasma Kit from Qiagen.
Figure 12C:
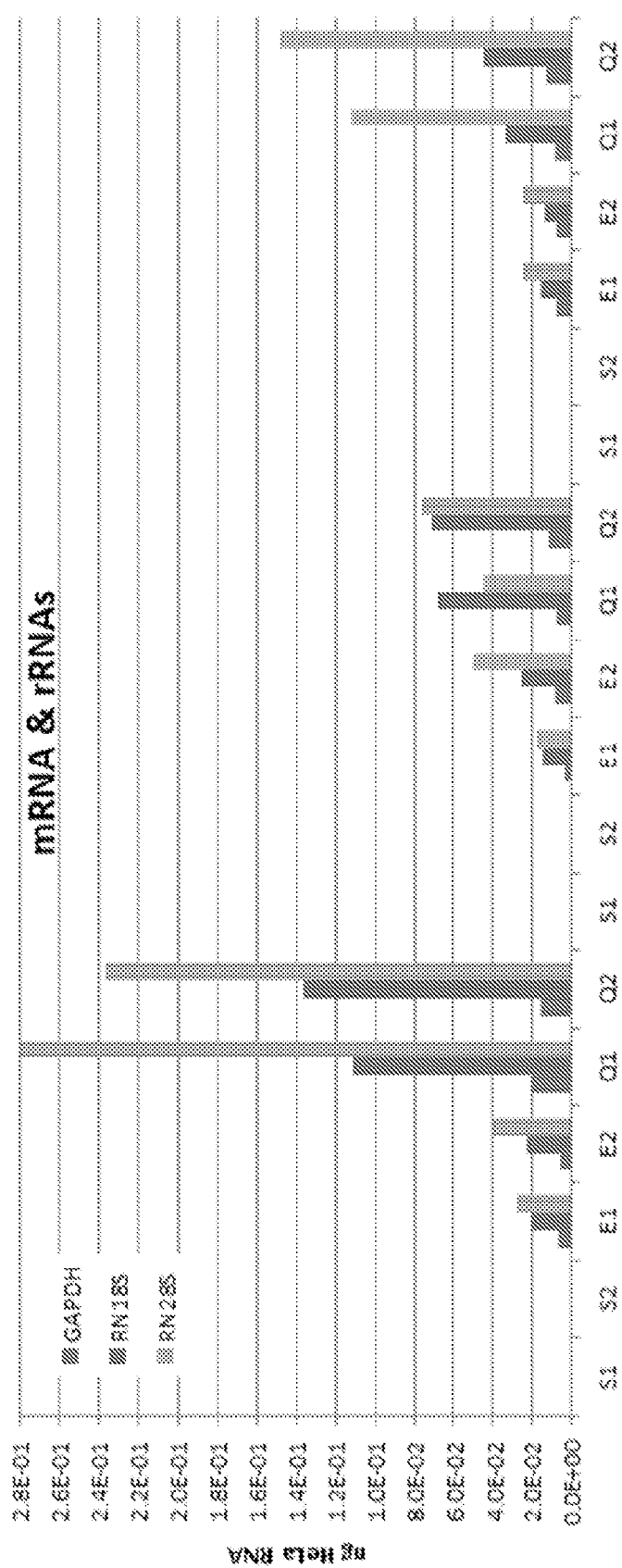
FIG. 12C shows the levels of GAPDH messenger RNA, RN18S ribosomal RNA, and RN28S ribosomal RNA isolated from plasma using Ago-RIP or column-based miRNA isolation kits. Three different experiments are presented. S1 and S2 represent isolation using Ago-RIP; E1 and E2 represent isolation using miRCury RNA Isolation Kit-Biofluids from Exiqon; and Q1 and Q2 represents isolation using miRNeasy Serum/Plasma Kit from Qiagen.

As expected, miRNAs such as let7a were isolated using Ago-RIP or either of the column-based kits (see FIG. 12A). However, other small RNAs or large RNAs were not isolated by Ago-RIP but were isolated with Exiqon and Qiagen kits. As shown in FIG. 12B and FIG. 12C, little or no RNU6, SNORD48, GAPDH, RN18S, or RN28S RNAS were isolated using Ago-RIP, but all of these other types of RNA were isolated with the Exiqon and Qiagen kits. Thus, Ago-RIP specifically isolates only miRNAs.

Example 13. Use of Both Anti-Ago1 and Anti-Ago2 Antibodies Increases RIP Yield

Since different miRNAs associate with different Ago proteins, it is possible that yields of certain miRNAs could be improved through the combined use of antibodies against different Ago proteins. Thus, miRNAs were isolated from 0.2 ml of plasma using 10 µg anti-Ago1 antibody/20 µl Protein A beads, 10 µg anti-Ago2 antibody/20 µl Protein A beads, or 20 µl of a 1:1 mixture of each type of antibody bead. Release of the miRNAs from the beads was performed using QIAzol lysis reagent and purified with the Qiagen kit essentially as described above in Example 3. Specific miRNAs (e.g., let7a, miR142-3p, miR122, miR191, and miR451a) were detected using MystiCq RT-qPCR assays.

Figure 13:
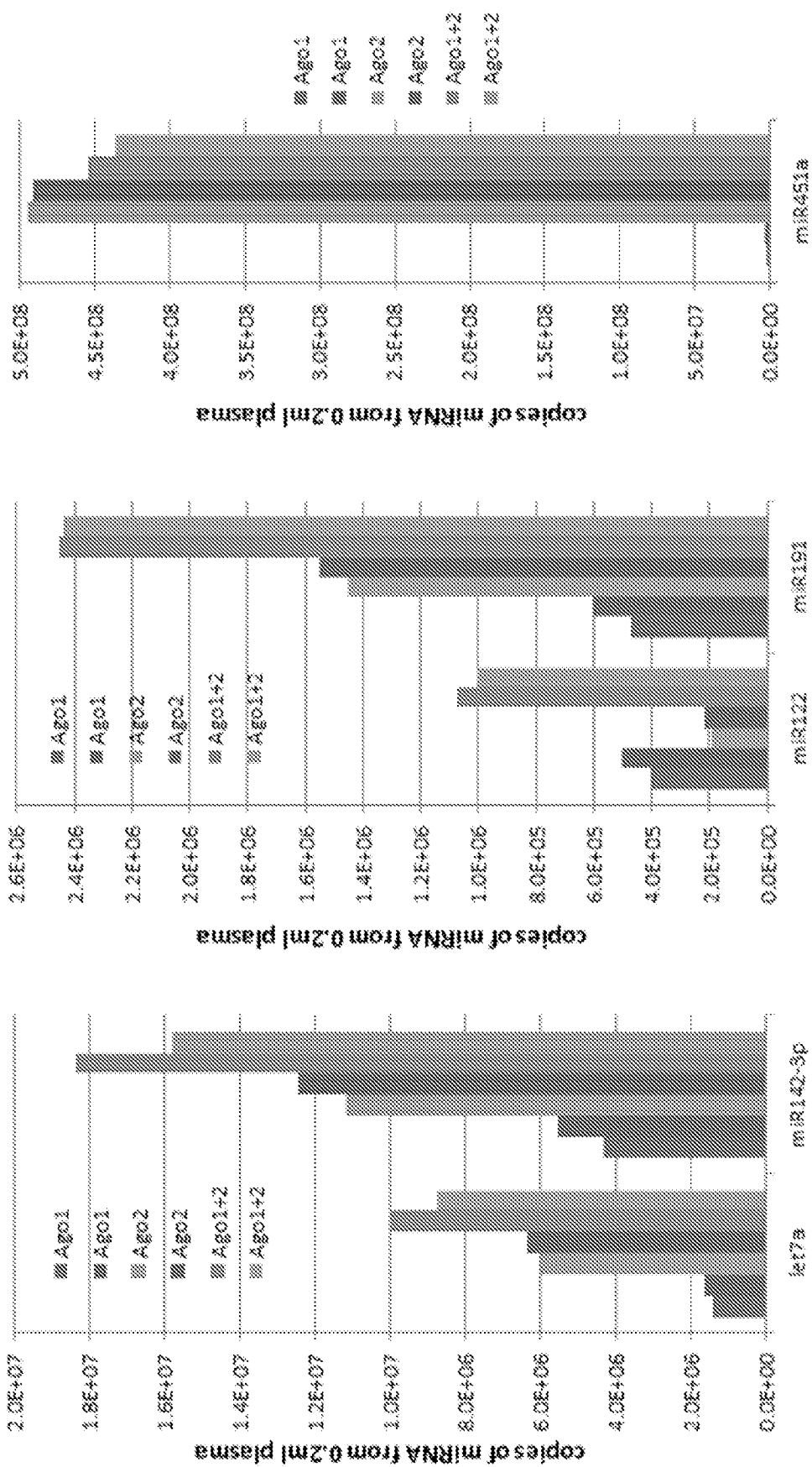
FIG. 13 presents a plot showing the levels of the indicated miRNAs isolated from plasma via Ago-RIP using anti-Ago1 antibodies, anti-Ago2 antibodies, or a combination of both anti-Ago1 and anti-Ago2 antibodies.

As shown in FIG. 13, yields using both antibodies together were approximately the sum of each antibody used separately. For most miRNAs, the use of anti-Ago2 resulted in a greater yield than use of anti-Ago1. However, more miR122 was recovered when anti-Ago1 was used, which is consistent with Turchinovich et al., 2012, RNA Biology 9(8):1066-75). Also, miR451a was only recovered with anti-Ago2, as explained above in Example 7.

What is claimed is:

1. A method for isolating microRNA (miRNA), the method comprising
   (a) contacting a biological sample with (i) at least one surface active agent selected from an anionic surfactant, a non-ionic surfactant, and combinations of anionic surfactants and/or non-ionic surfactants; (ii) an anti-Argonaut antibody, wherein the surface active agent dissociates biological sample components and the anti-miRNA-binding protein reagent interacts with a miRNA-binding protein associated with miRNA to form immunoprecipitated miRNA complexes, and wherein the biological sample, the at least one surface active agent, and the anti-Argonaut antibody are contacted at room temperature; and
   (b) contacting the immunoprecipitated miRNA complexes a proteinase K at room temperature to release miRNA from the immunoprecipitated miRNA complexes without purification.

2. The method of claim 1, wherein the biological sample comprises vesicular miRNA and non-vesicular miRNA.

3. The method of claim 1, wherein the biological sample comprises a tissue sample.

4. The method of claim 1, wherein the at least one surface active agent selected from polyoxyethylene (20) sorbitol monolaurate (TWEEN® 20); polyoxyethylene (20) sorbitol monopalmitate (TWEEN® 40); polyoxyethylene (20) sorbitol monooleate (TWEEN® 80); sodium deoxycholate, sodium lauryl sulfate, and combinations thereof.

5. The method of claim 1, wherein the biological fluid sample is contacted with the at least one surface active agent and the anti-Argonaut antibody simultaneously.

6. The method of claim 1, wherein the biological sample, the at least one surface active agent, and the anti-Argonaut antibody are incubated for about 30 minutes.

7. The method of claim 1, wherein the anti-Argonaut antibody is attached to a solid support.

8. The method of claim 7, wherein the solid support is magnetic beads.

9. The method of claim 1, wherein anti-Argonaut antibody is capable of binding Ago1, Ago2, Ago3, and/or Ago4.

10. The method of claim 1, wherein contact with the proteinase K proceeds for about 10 minutes.

11. The method of claim 1, wherein the miRNA released from the immunoprecipitated miRNA complexes is free of other types of RNA molecules.

\* \* \* \* \*

UNITED STATES PATENT AND TRADEMARK OFFICE
CERTIFICATE OF CORRECTION

PATENT NO. : 10,711,266 B2
APPLICATION NO. : 16/160363
DATED : July 14, 2020
INVENTOR(S) : Carol A. Kreader Page 1 of 1

It is certified that error appears in the above-identified patent and that said Letters Patent is hereby corrected as shown below:

On the Title Page

Item (60), insert -- Provisional application No. 61/985,000, filed on April 28, 2014 --.

In the Claims

In Column 23, on Line 9, in Claim 5, delete "fluid".

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*